United States Patent
Poltaretskyi et al.

(10) Patent No.: US 12,042,341 B2
(45) Date of Patent: Jul. 23, 2024

(54) REGISTRATION MARKER WITH ANTI-ROTATION BASE FOR ORTHOPEDIC SURGICAL PROCEDURES

(71) Applicant: HOWMEDICA OSTEONICS CORP., Mahwah, NJ (US)

(72) Inventors: Sergii Poltaretskyi, Plougonvelin (FR); Vincent Abel Maurice Simoes, Locmaria Plouzané (FR); Nicolas Neichel, Le Sappey en Chartreuse (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 388 days.

(21) Appl. No.: 17/243,053

(22) Filed: Apr. 28, 2021

(65) Prior Publication Data
US 2021/0346117 A1    Nov. 11, 2021

Related U.S. Application Data

(60) Provisional application No. 63/020,800, filed on May 6, 2020.

(51) Int. Cl.
*A61B 17/84* (2006.01)
*A61B 90/00* (2016.01)
*A61B 34/10* (2016.01)

(52) U.S. Cl.
CPC ............ *A61B 90/39* (2016.02); *A61B 17/846* (2013.01); *A61B 90/36* (2016.02); *A61B 2034/107* (2016.02); *A61B 2090/364* (2016.02); *A61B 2090/3916* (2016.02); *A61B 2090/3983* (2016.02); *A61B 2090/3991* (2016.02)

(58) Field of Classification Search
CPC ....... A61B 17/84; A61B 17/846; A61B 90/00; A61B 90/39; A61B 90/36
See application file for complete search history.

(56) References Cited

U.S. PATENT DOCUMENTS

| | | |
|---|---|---|
| 7,715,602 B2 | 5/2010 | Richard |
| 7,857,821 B2 | 12/2010 | Couture et al. |
| 8,147,496 B2 | 4/2012 | Couture et al. |
| 8,506,645 B2 | 8/2013 | Blaylock et al. |
| 9,767,608 B2 | 9/2017 | Lee et al. |
| 10,278,777 B1 | 5/2019 | Lang |

(Continued)

OTHER PUBLICATIONS

Boissonnat, "Shape Reconstruction from Planar Cross Sections," Computer Vision, Graphics and Image Processing, Academic Press, Inc, Mar. 29, 1988, 29 pp.

(Continued)

*Primary Examiner* — Christopher J Beccia
(74) *Attorney, Agent, or Firm* — Shumaker & Sieffert, P.A.

(57) ABSTRACT

Bone tracking during orthopedic surgical procedures is described herein. An anti-rotation base of a registration marker of a mixed reality surgery system includes a surface configured to rest on and bear against a surface of a glenoid of a patient. The anti-rotation base also includes a plurality of pin receptacles that each define a respective pin axis. The pin axis of a first pin receptacle of the plurality of pin receptacles is not parallel to the pin axis of a second pin receptacle of the plurality of pin receptacles. Additionally, the anti-rotation base includes a mounting receptacle configured to receive the registration marker.

16 Claims, 13 Drawing Sheets

(56) References Cited

U.S. PATENT DOCUMENTS

| | | |
|---|---|---|
| 10,326,975 B2 | 6/2019 | Casas |
| 10,426,549 B2 | 10/2019 | Kehres et al. |
| 10,881,462 B2 | 1/2021 | Heavener et al. |
| 11,553,969 B1 * | 1/2023 | Lang ............... G06T 7/0012 |
| 2012/0143267 A1 * | 6/2012 | Iannotti ............. A61B 17/151 |
| | | 606/86 R |
| 2016/0074052 A1 * | 3/2016 | Keppler ........... A61B 17/1778 |
| | | 606/87 |
| 2018/0049622 A1 * | 2/2018 | Ryan .................... A61B 90/37 |
| 2018/0263670 A1 * | 9/2018 | Moctezuma De la Barrera ......... |
| | | A61B 17/809 |
| 2019/0192230 A1 | 6/2019 | Siemionow et al. |
| 2020/0170751 A1 * | 6/2020 | Pack ................... A61B 90/39 |
| 2020/0383803 A1 * | 12/2020 | Wu ..................... A61B 6/5217 |

OTHER PUBLICATIONS

Marker et al., "Contour-Based Surface Reconstruction using Implicit Curve Fitting, and Distance Field Filtering and Interpolation," The Eurographics Association, Jul. 2006, 9 pp.

Nguyen et al., "A new segmentation method for MRI images of the shoulder joint," Fourth Canadian Conference on Computer and Robot Vision(CRV'07), IEEE Computer Society, May 28-30, 2007, 8 pp.

* cited by examiner

REGISTRATION MARKER WITH ANTI-ROTATION BASE FOR ORTHOPEDIC SURGICAL PROCEDURES

This application claims the benefit of U.S. Provisional Patent Application No. 63/020,800, filed 6 May 2020, the entire contents of which is incorporated herein by reference.

TECHNICAL FIELD

This disclosure relates to bone tracking during orthopedic surgical procedures.

BACKGROUND

Surgical joint repair procedures involve repair and/or replacement of a damaged or diseased joint. Many times, a surgical joint repair procedure, such as joint arthroplasty as an example, involves replacing the damaged joint with a prosthetic that is implanted into the patient's bone. Proper selection of a prosthetic that is appropriately sized and shaped and proper positioning of that prosthetic to ensure an optimal surgical outcome can be challenging. To assist with positioning, the surgical procedure often involves the use of surgical instruments to control the shaping of the surface of the damaged bone and cutting or drilling of bone to accept the prosthetic.

Virtual visualization tools are available to surgeons that use three-dimensional modeling of bone shapes to facilitate preoperative planning for joint repairs and replacements. These tools can assist surgeons with the design and/or selection of surgical guides and implants that closely match the patient's anatomy and can improve surgical outcomes by customizing a surgical plan for each patient.

SUMMARY

This disclosure describes a variety of techniques for intra-operative surgical guidance using mixed reality (MR)-based visualization for surgical joint repair procedures. The techniques may be used independently or in various combinations to support particular phases or settings for surgical joint repair procedures or provide a multi-faceted ecosystem to support surgical joint repair procedures. As described below, a registration marker is affixed to bone of a patient by an anti-rotation based. A three-dimensional geometric marker is mounted on anchor pin fixed in an anti-rotation base configured to rest on and bear against surface of the bone (e.g., a superior region of glenoid, etc.) to resist rotation. In some examples, the anti-rotation base is designed to conform to patient-specific anatomy to promote proper orientation. In some examples, the anti-rotation base defines anchor holes are offset relative to each other so that the anchor rods do not interfere with each other. The registration marker provides a reference for a transformation matrix used to align virtual objects (e.g., virtual images of a glenoid, etc.) to their corresponding physical objects.

An anti-rotation base of a registration marker of a mixed reality surgery system may include a surface configured to rest on and bear against a surface of a glenoid of a patient. The anti-rotation base may also include a plurality of pin receptacles that each define a respective pin axis. The pin axis of a first pin receptacle of the plurality of pin receptacles may not be parallel to the pin axis of a second pin receptacle of the plurality of pin receptacles. Additionally, the anti-rotation base may include a mounting receptacle configured to receive the registration marker.

The details of various examples of the disclosure are set forth in the accompanying drawings and the description below. Various features, objects, and advantages will be apparent from the description, drawings, and claims.

DETAILED DESCRIPTION

Figure 1:
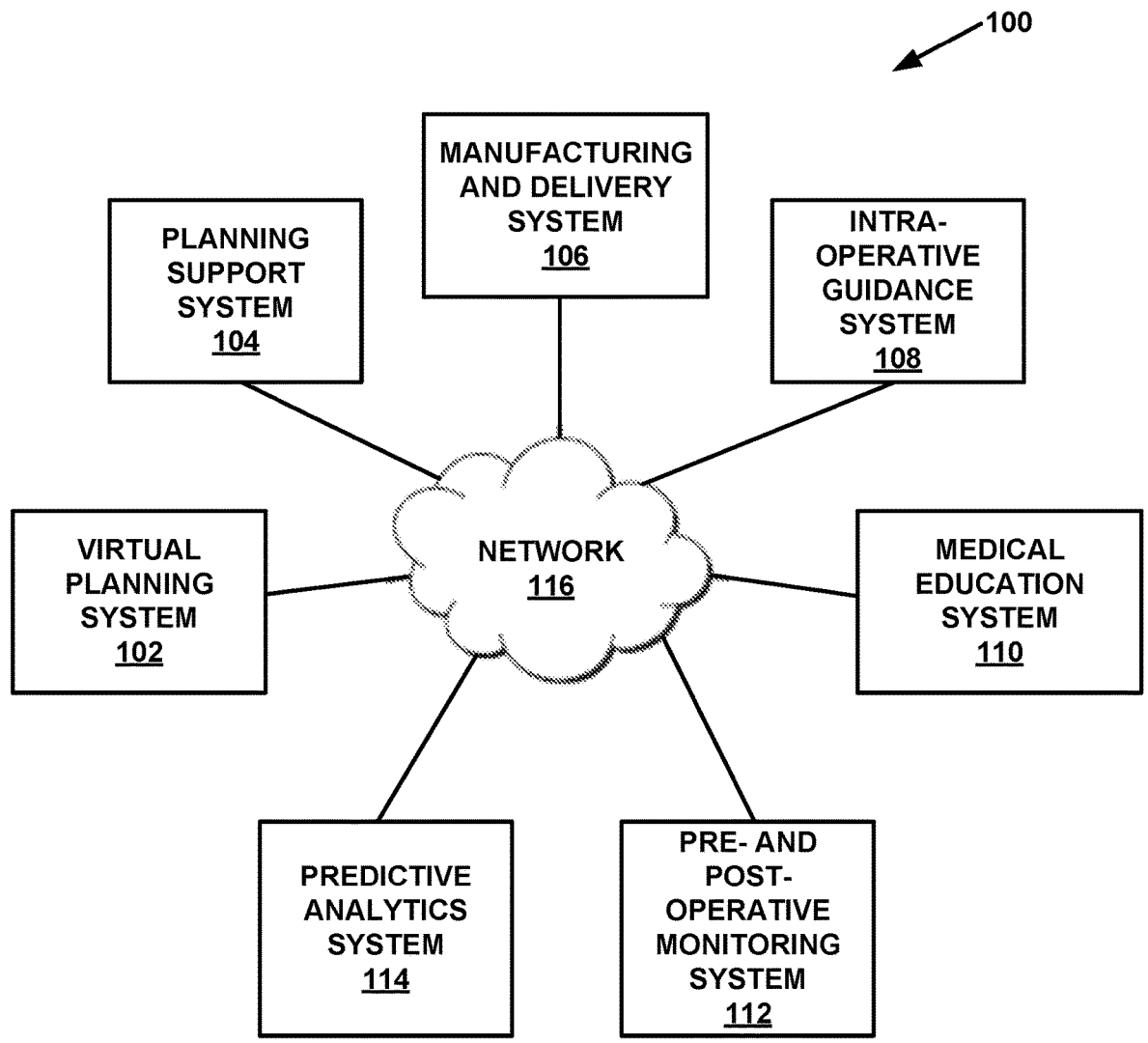
FIG. 1 is a block diagram of an orthopedic surgical system according to an example of this disclosure.

The disclosure is directed to a registration marker to attach a fiducial marker to a bone (e.g., a glenoid, etc.) in a patient to provide a reference for a transformation matrix used in a mixed reality system. The apparatus includes an anti-rotation base, a mounting rod, and the fiducial marker. In some examples, the anti-rotation based defines an arch configured to rest on and bear against a surface of the bone (e.g., a superior region of the glenoid, etc.). The anti-rotation base also defines a mount hole to slidably couple the anti-rotation base to the mounting rod. The arch is configured to straddle a portion of the bone on which the apparatus will be mounted. The mounting hole is configured to accommodate the mounting rod such that the mounting rod, when installed, passes through the bridge. In some examples, the mounting rod terminates in an attachment end to anchor the mounting rod to the bone. Additionally, in some examples, the anti-rotation base defines at least two anchor holes (sometimes referred to as "pin holes" or "pin receptacles"). The anchor holes are configured to, when installed, accommodate anchor rods (sometimes referred to as "pins") that fix the orientation of the bridge to prevent movement of the apparatus. The anchor holes are offset relative to each other so that the anchor rods, when installed, do not interfere with each other. The example fiducial marker is a polyhedron with a pattern recognizable by a computer vision system (e.g., a QR code, a bar code, an image, etc.) on one or more faces to facilitate aligning an orientation of patient with the orientation of the image(s) to be overlaid via the mixed reality system. The fiducial marker is affixed to the end of the mounting rod such that, when installed, the fiducial marker is spaced away from the surface of the patient.

The registration maker is used with a mixed reality (MR) visualization system to assist with creation, implementation, verification, and/or modification of a surgical plan before and during a surgical procedure. Because MR, or in some instances VR, may be used to interact with the surgical plan, this disclosure may also refer to the surgical plan as a "virtual" surgical plan. Visualization tools other than or in addition to mixed reality visualization systems may be used in accordance with techniques of this disclosure. A surgical plan, e.g., as generated by the BLUEPRINT™ system, available from Wright Medical Group, N.V., or another surgical planning platform, may include information defining a variety of features of a surgical procedure, such as features of particular surgical procedure steps to be performed on a patient by a surgeon according to the surgical plan including, for example, bone or tissue preparation steps and/or steps for selection, modification and/or placement of implant components. Such information may include, in various examples, dimensions, shapes, angles, surface contours, and/or orientations of implant components to be selected or modified by surgeons, dimensions, shapes, angles, surface contours and/or orientations to be defined in bone or tissue by the surgeon in bone or tissue preparation steps, and/or positions, axes, planes, angle and/or entry points defining placement of implant components by the surgeon relative to patient bone or tissue. Information such as dimensions, shapes, angles, surface contours, and/or orientations of anatomical features of the patient may be derived from imaging (e.g., x-ray, CT, MRI, ultrasound or other images), direct observation, or other techniques. In some examples, the virtual In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which they are presented as coexisting. In addition, virtual objects described in various examples of this disclosure may include graphics, images, animations or videos, e.g., presented as 3D virtual objects or 2D virtual objects. Virtual objects may also be referred to as virtual elements. Such elements may or may not be analogs of real-world objects. In some examples, in mixed reality, a camera may capture images of the real world and modify the images to present virtual objects in the context of the real world. In such examples, the modified images may be displayed on a screen, which may be head-mounted, hand-held, or otherwise viewable by a user. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects.

The Microsoft HOLOLENS™ headset, available from Microsoft Corporation of Redmond, Washington, is an example of a MR device that includes see-through holographic lenses, sometimes referred to as waveguides, that permit a user to view real-world objects through the lens and concurrently view projected 3D holographic objects. The Microsoft HOLOLENS™ headset, or similar waveguide-based visualization devices, are examples of an MR visualization device that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively-brightened areas may be considered virtual objects superimposed on the parts of the user's physical environment that are in shadow.

Furthermore, in this disclosure, the term "virtual reality" (VR) refers to an immersive artificial environment that a user experiences through sensory stimuli (such as sights and sounds) provided by a computer. Thus, in virtual reality, the user may not see any physical objects as they exist in the real world. Video games set in imaginary worlds are a common example of VR. The term "VR" also encompasses scenarios where the user is presented with a fully artificial environment in which some virtual object's locations are based on the locations of corresponding physical objects as they relate to the user. Walk-through VR attractions are examples of this type of VR.

The term "extended reality" (XR) is a term that encompasses a spectrum of user experiences that includes virtual reality, mixed reality, augmented reality, and other user experiences that involve the presentation of at least some perceptible elements as existing in the user's environment that are not present in the user's real-world environment. Thus, the term "extended reality" may be considered a genus for MR and VR. XR visualizations may be presented in any of the techniques for presenting mixed reality discussed elsewhere in this disclosure or presented using techniques for presenting VR, such as VR goggles.

Visualization tools are available that utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Group, N.V. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

FIG. 1 is a block diagram of an orthopedic surgical system 100 according to an example of this disclosure. Orthopedic surgical system 100 includes a set of subsystems. In the example of FIG. 1, the subsystems include a virtual planning system 102, a planning support system 104, a manufacturing and delivery system 106, an intraoperative guidance system 108, a medical education system 110, a monitoring system 112, a predictive analytics system 114, and a communications network 116. In other examples, orthopedic surgical system 100 may include more, fewer, or different subsystems. For example, orthopedic surgical system 100 may omit medical education system 110, monitor system 112, predictive analytics system 114, and/or other subsystems. In some examples, orthopedic surgical system 100 may be used for surgical tracking, in which case orthopedic surgical system 100 may be referred to as a surgical tracking system. In other cases, orthopedic surgical system 100 may be generally referred to as a medical device system.

Users of orthopedic surgical system 100 may use virtual planning system 102 to plan orthopedic surgeries. Users of orthopedic surgical system 100 may use planning support system 104 to review surgical plans generated using orthopedic surgical system 100. Manufacturing and delivery system 106 may assist with the manufacture and delivery of items needed to perform orthopedic surgeries. Intraoperative guidance system 108 provides guidance to assist users of orthopedic surgical system 100 in performing orthopedic surgeries. Medical education system 110 may assist with the education of users, such as healthcare professionals, patients, and other types of individuals. Pre- and postoperative monitoring system 112 may assist with monitoring patients before and after the patients undergo surgery. Predictive analytics system 114 may assist healthcare professionals with various types of predictions. For example, predictive analytics system 114 may apply artificial intelligence techniques to determine a classification of a condition of an orthopedic joint, e.g., a diagnosis, determine which type of surgery to perform on a patient and/or which type of implant to be used in the procedure, determine types of items that may be needed during the surgery, and so on.

The subsystems of orthopedic surgical system 100 (i.e., virtual planning system 102, planning support system 104, manufacturing and delivery system 106, intraoperative guidance system 108, medical education system 110, pre- and postoperative monitoring system 112, and predictive analytics system 114) may include various systems. The systems in the subsystems of orthopedic surgical system 100 may include various types of computing systems, computing devices, including server computers, personal computers, tablet computers, smartphones, display devices, Internet of Things (IoT) devices, visualization devices (e.g., mixed reality (MR) visualization devices, virtual reality (VR) visualization devices, holographic projectors, or other devices for presenting extended reality (XR) visualizations), surgical tools, and so on. A holographic projector, in some examples, may project a hologram for general viewing by multiple users or a single user without a headset, rather than viewing only by a user wearing a headset. For example, virtual planning system 102 may include a MR visualization device and one or more server devices, planning support system 104 may include one or more personal computers and one or more server devices, and so on. A computing system is a set of one or more computing systems configured to operate as a system. In some examples, one or more devices may be shared between the two or more of the subsystems of orthopedic surgical system 100. For instance, in the previous examples, virtual planning system 102 and planning support system 104 may include the same server devices.

In the example of FIG. 1, the devices included in the subsystems of orthopedic surgical system 100 may communicate using communication network 116. Communication network 116 may include various types of communication networks including one or more wide-area networks, such as the Internet, local area networks, and so on. In some examples, communication network 116 may include wired and/or wireless communication links.

Figure 2:
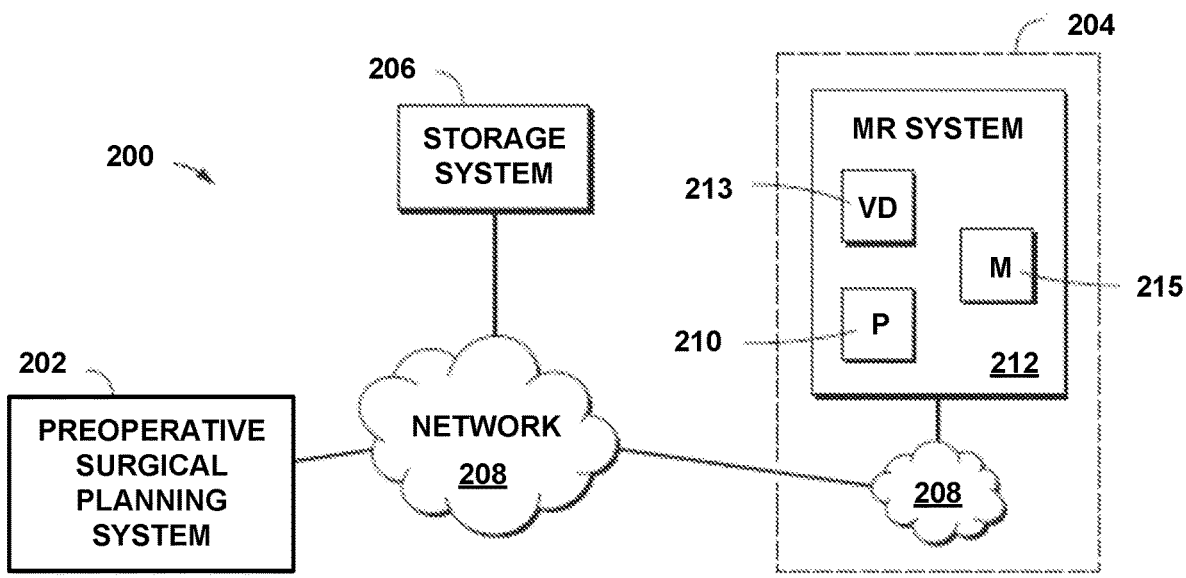
FIG. 2 is a block diagram of an orthopedic surgical system that includes a mixed reality (MR) system, according to an example of this disclosure.

Many variations of orthopedic surgical system 100 are possible in accordance with techniques of this disclosure. Such variations may include more or fewer subsystems than the version of orthopedic surgical system 100 shown in FIG. 1. For example, FIG. 2 is a block diagram of an orthopedic surgical system 200 that includes one or more mixed reality (MR) systems, according to an example of this disclosure. Orthopedic surgical system 200 may be used for creating, verifying, updating, modifying and/or implementing a surgical plan. In some examples, the surgical plan can be created preoperatively, such as by using a virtual surgical planning system (e.g., the BLUEPRINT™ system), and then verified, modified, updated, and viewed intraoperatively, e.g., using MR visualization of the surgical plan. In other examples, orthopedic surgical system 200 can be used to create the surgical plan immediately prior to surgery or intraoperatively, as needed. In some examples, orthopedic surgical system 200 may be used for surgical tracking, in which case orthopedic surgical system 200 may be referred to as a surgical tracking system. In other cases, orthopedic surgical system 200 may be generally referred to as a medical device system.

In the example of FIG. 2, orthopedic surgical system 200 includes a preoperative surgical planning system 202, a healthcare facility 204 (e.g., a surgical center or hospital), a storage system 206 and a network 208 that allows a user at healthcare facility 204 to access stored patient information, such as medical history, image data corresponding to the damaged joint or bone and various parameters corresponding to a surgical plan that has been created preoperatively (as examples). Preoperative surgical planning system 202 may be equivalent to virtual planning system 102 of FIG. 1 and, in some examples, may generally correspond to a virtual planning system similar or identical to the BLUEPRINT™ system.

In the example of FIG. 2, healthcare facility 204 includes a mixed reality (MR) system 212. In some examples of this disclosure, MR system 212 includes one or more processing device(s) (P) 210 to provide functionalities that will be described in further detail below. Processing device(s) 210 may also be referred to as processor(s). In addition, one or more users of MR system 212 (e.g., a surgeon, nurse, or other care provider) can use processing device(s) (P) 210 to generate a request for a particular surgical plan or other patient information that is transmitted to storage system 206 via network 208. In response, storage system 206 returns the requested patient information to MR system 212. In some examples, the users can use other processing device(s) to request and receive information, such as one or more processing devices that are part of MR system 212, but not part of any visualization device, or one or more processing devices that are part of a visualization device (e.g., visualization device 213) of MR system 212, or a combination of one or more processing devices that are part of MR system 212, but not part of any visualization device, and one or more processing devices that are part of a visualization device (e.g., visualization device 213) that is part of MR system 212.

In some examples, multiple users can simultaneously use MR system 212. For example, MR system 212 can be used in a spectator mode in which multiple users each use their own visualization devices so that the users can view the same information at the same time and from the same point of view. In some examples, MR system 212 may be used in a mode in which multiple users each use their own visualization devices so that the users can view the same information from different points of view.

In some examples, processing device(s) 210 can provide a user interface to display data and receive input from users at healthcare facility 204. Processing device(s) 210 may be configured to control visualization device 213 to present a user interface. Furthermore, processing device(s) 210 may be configured to control visualization device 213 to present virtual images, such as 3D virtual models, 2D images, and so on. Processing device(s) 210 can include a variety of different processing or computing devices, such as servers, desktop computers, laptop computers, tablets, mobile phones and other electronic computing devices, or processors within such devices. In some examples, one or more of processing device(s) 210 can be located remote from healthcare facility 204. In some examples, processing device(s) 210 reside within visualization device 213. In some examples, at least one of processing device(s) 210 is external to visualization device 213. In some examples, one or more processing device(s) 210 reside within visualization device 213 and one or more of processing device(s) 210 are external to visualization device 213.

In the example of FIG. 2, MR system 212 also includes one or more memory or storage device(s) (M) 215 for storing data and instructions of software that can be executed by processing device(s) 210. The instructions of software can correspond to the functionality of MR system 212 described herein. In some examples, the functionalities of a virtual surgical planning application, such as the BLUE-PRINT™ system, can also be stored and executed by processing device(s) 210 in conjunction with memory storage device(s) (M) 215. For instance, memory or storage system 215 may be configured to store data corresponding to at least a portion of a virtual surgical plan. In some examples, storage system 206 may be configured to store data corresponding to at least a portion of a virtual surgical plan. In some examples, memory or storage device(s) (M) 215 reside within visualization device 213. In some examples, memory or storage device(s) (M) 215 are external to visualization device 213. In some examples, memory or storage device(s) (M) 215 include a combination of one or more memory or storage devices within visualization device 213 and one or more memory or storage devices external to the visualization device.

Network 208 may be equivalent to network 116. Network 208 can include one or more wide area networks, local area networks, and/or global networks (e.g., the Internet) that connect preoperative surgical planning system 202 and MR system 212 to storage system 206. Storage system 206 can include one or more databases that can contain patient information, medical information, patient image data, and parameters that define the surgical plans. For example, medical images of the patient's diseased or damaged bone typically are generated preoperatively in preparation for an orthopedic surgical procedure. The medical images can include images of the relevant bone(s) taken along the sagittal plane and the coronal plane of the patient's body. The medical images can include X-ray images, magnetic resonance imaging (MRI) images, computerized tomography (CT) images, ultrasound images, and/or any other type of 2D or 3D image that provides information about the relevant surgical area. Storage system 206 also can include data identifying the implant components selected for a particular patient (e.g., type, size, etc.), surgical guides selected for a particular patient, and details of the surgical procedure, such as entry points, cutting planes, drilling axes, reaming depths, etc. Storage system 206 can be a cloud-based storage system (as shown) or can be located at healthcare facility 204 or at the location of preoperative surgical planning system 202 or can be part of MR system 212 or visualization device (VD) 213, as examples.

MR system 212 can be used by a surgeon before (e.g., preoperatively) or during the surgical procedure (e.g., intraoperatively) to create, review, verify, update, modify and/or implement a surgical plan. In some examples, MR system 212 may also be used after the surgical procedure (e.g., postoperatively) to review the results of the surgical procedure, assess whether revisions are required, or perform other postoperative tasks. To that end, MR system 212 may include a visualization device 213 that may be worn by the surgeon and (as will be explained in further detail below) is operable to display a variety of types of information, including a 3D virtual image of the patient's diseased, damaged, or postsurgical joint and details of the surgical plan, such as a 3D virtual image of the prosthetic implant components selected for the surgical plan, 3D virtual images of entry points for positioning the prosthetic components, alignment axes and cutting planes for aligning cutting or reaming tools to shape the bone surfaces, or drilling tools to define one or more holes in the bone surfaces, in the surgical procedure to properly orient and position the prosthetic components, surgical guides and instruments and their placement on the damaged joint, and any other information that may be useful to the surgeon to implement the surgical plan. MR system 212 can generate images of this information that are perceptible to the user of the visualization device 213 before and/or during the surgical procedure.

In some examples, MR system 212 includes multiple visualization devices (e.g., multiple instances of visualization device 213) so that multiple users can simultaneously see the same images and share the same 3D scene. In some such examples, one of the visualization devices can be designated as the master device and the other visualization devices can be designated as observers or spectators. Any observer device can be re-designated as the master device at any time, as may be desired by the users of MR system 212.

In this way, FIG. 2 illustrates a surgical planning system that includes a preoperative surgical planning system 202 to generate a virtual surgical plan customized to repair an anatomy of interest of a particular patient. For example, the virtual surgical plan may include a plan for an orthopedic joint repair surgical procedure, such as one of a standard total shoulder arthroplasty or a reverse shoulder arthroplasty. In this example, details of the virtual surgical plan may include details relating to at least one of preparation of glenoid bone or preparation of humeral bone. In some examples, the orthopedic joint repair surgical procedure is one of a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, and an augmented glenoid reverse shoulder arthroplasty.

The virtual surgical plan may include a 3D virtual model corresponding to the anatomy of interest of the particular patient, a 3D model of one or more tools, and/or a 3D model of a prosthetic component matched to the particular patient to repair the anatomy of interest or selected to repair the anatomy of interest. In some examples, the 3D model may include a point cloud or mesh (e.g., polygonal mesh, wireframe, etc.) that represents a feature of the corresponding object. As one example, a 3D model of a patient's bone may include a point cloud or mesh that represents a wall of the bone. As another example, a 3D model of a patient's bone may include a first point cloud or mesh that represents an inner wall of the bone and a second point cloud or mesh that represents an outer wall of the bone. As another example, a 3D model of a prosthetic component (e.g., an implant) may include a point cloud or mesh that represents an outer surface of at least a portion of the prosthetic component (e.g., the portion that is inserted into the bone). As another example, a 3D model of an implant tool may include a point cloud or mesh that represents an outer surface of at least a portion of the implant tool (e.g., the portion that is inserted into the bone).

Furthermore, in the example of FIG. 2, the surgical planning system includes a storage system 206 to store data corresponding to the virtual surgical plan. The surgical planning system of FIG. 2 also includes MR system 212, which may comprise visualization device 213. In some examples, visualization device 213 is wearable by a user. In some examples, visualization device 213 is held by a user, or rests on a surface in a place accessible to the user. MR system 212 may be configured to present a user interface via visualization device 213. The user interface is visually perceptible to the user using visualization device 213. For instance, in one example, a screen of visualization device 213 may display real-world images and the user interface on a screen. In some examples, visualization device 213 may project virtual, holographic images onto see-through holographic lenses and also permit a user to see real-world objects of a real-world environment through the lenses. In other words, visualization device 213 may comprise one or more see-through holographic lenses and one or more display devices that present imagery to the user via the holographic lenses to present the user interface to the user.

In some examples, visualization device 213 is configured such that the user can manipulate the user interface (which is visually perceptible to the user when the user is wearing or otherwise using visualization device 213) to request and view details of the virtual surgical plan for the particular patient, including a 3D virtual model of the anatomy of interest (e.g., a 3D virtual bone of the anatomy of interest) and a 3D model of the prosthetic component selected to repair an anatomy of interest. In some such examples, visualization device 213 is configured such that the user can manipulate the user interface so that the user can view the virtual surgical plan intraoperatively, including (at least in some examples) the 3D virtual model of the anatomy of interest (e.g., a 3D virtual bone of the anatomy of interest). In some examples, MR system 212 can be operated in an augmented surgery mode in which the user can manipulate the user interface intraoperatively so that the user can visually perceive details of the virtual surgical plan projected in a real environment, e.g., on a real anatomy of interest of the particular patient. In this disclosure, the terms real and real world may be used in a similar manner. For example, MR system 212 may present one or more virtual objects that provide guidance for preparation of a bone surface and placement of a prosthetic implant on the bone surface. Visualization device 213 may present one or more virtual objects in a manner in which the virtual objects appear to be overlaid on an actual, real anatomical object of the patient, within a real-world environment, e.g., by displaying the virtual object(s) with actual, real-world patient anatomy viewed by the user through holographic lenses. For example, the virtual objects may be 3D virtual objects that appear to reside within the real-world environment with the actual, real anatomical object.

Figure 3:
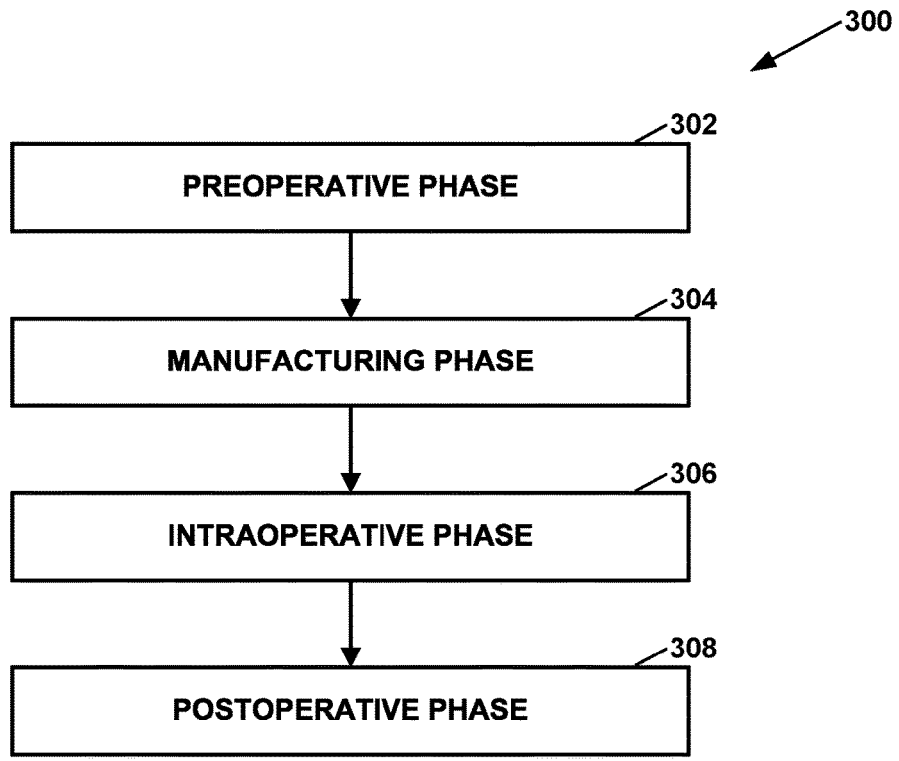
FIG. 3 is a flowchart illustrating example phases of a surgical lifecycle.

FIG. 3 is a flowchart illustrating example phases of a surgical lifecycle 300. In the example of FIG. 3, surgical lifecycle 300 begins with a preoperative phase (302). During the preoperative phase, a surgical plan is developed. The preoperative phase is followed by a manufacturing and delivery phase (304). During the manufacturing and delivery phase, patient-specific items, such as parts and equipment, needed for executing the surgical plan are manufactured and delivered to a surgical site. In some examples, it is unnecessary to manufacture patient-specific items in order to execute the surgical plan. An intraoperative phase follows the manufacturing and delivery phase (306). The surgical plan is executed during the intraoperative phase. In other words, one or more persons perform the surgery on the patient during the intraoperative phase. The intraoperative phase is followed by the postoperative phase (308). The postoperative phase includes activities occurring after the surgical plan is complete. For example, the patient may be monitored during the postoperative phase for complications.

As described in this disclosure, orthopedic surgical system 100 (FIG. 1) may be used in one or more of preoperative phase 302, the manufacturing and delivery phase 304, the intraoperative phase 306, and the postoperative phase 308. For example, virtual planning system 102 and planning support system 104 may be used in preoperative phase 302. Manufacturing and delivery system 106 may be used in the manufacturing and delivery phase 304. Intraoperative guidance system 108 may be used in intraoperative phase 306. Some of the systems of FIG. 1 may be used in multiple phases of FIG. 3. For example, medical education system 110 may be used in one or more of preoperative phase 302, intraoperative phase 306, and postoperative phase 308; pre- and postoperative monitoring system 112 may be used in preoperative phase 302 and postoperative phase 308. Predictive analytics system 114 may be used in preoperative phase 302 and postoperative phase 308.

As mentioned above, one or more of the subsystems of orthopedic surgical system 100 may include one or more mixed reality (MR) systems, such as MR system 212 (FIG.

2). Each MR system may include a visualization device. For instance, in the example of FIG. 2, MR system 212 includes visualization device 213. In some examples, in addition to including a visualization device, an MR system may include external computing resources that support the operations of the visualization device. For instance, the visualization device of an MR system may be communicatively coupled to a computing device (e.g., a personal computer, backpack computer, smartphone, etc.) that provides the external computing resources. Alternatively, adequate computing resources may be provided on or within visualization device 213 to perform necessary functions of the visualization device.

Figure 4:
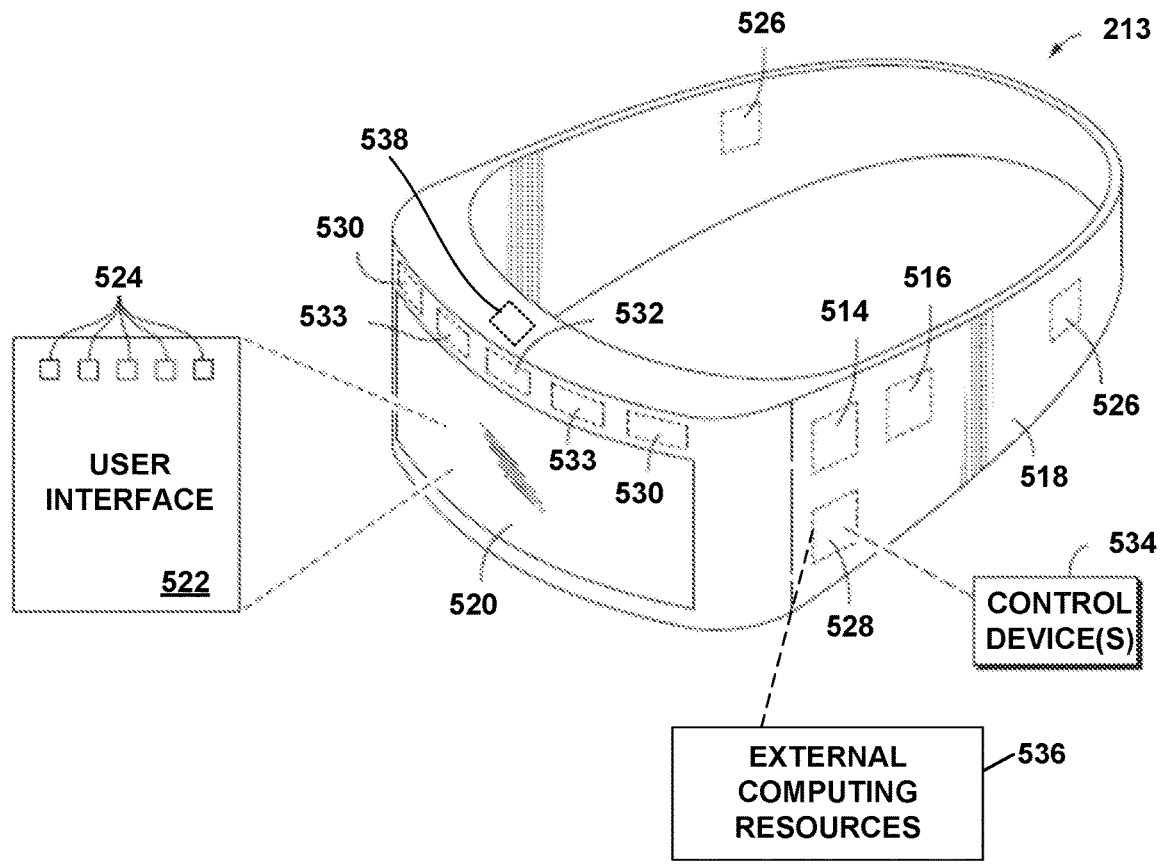
FIG. 4 is a schematic representation of a visualization device for use in a mixed reality (MR) system, according to an example of this disclosure.

FIG. 4 is a schematic representation of visualization device 213 for use in an MR system, such as MR system 212 of FIG. 2, according to an example of this disclosure. As shown in the example of FIG. 4, visualization device 213 can include a variety of electronic components found in a computing system, including one or more processor(s) 514 (e.g., microprocessors or other types of processing units) and memory 516 that may be mounted on or within a frame 518. Furthermore, in the example of FIG. 4, visualization device 213 may include a transparent screen 520 that is positioned at eye level when visualization device 213 is worn by a user. In some examples, screen 520 can include one or more liquid crystal displays (LCDs) or other types of display screens on which images are perceptible to a surgeon who is wearing or otherwise using visualization device 213 via screen 520. Other display examples include organic light emitting diode (OLED) displays. In some examples, visualization device 213 can operate to project 3D images onto the user's retinas using techniques known in the art.

In some examples, screen 520 may include see-through holographic lenses. sometimes referred to as waveguides, that permit a user to see real-world objects through (e.g., beyond) the lenses and also see holographic imagery projected into the lenses and onto the user's retinas by displays, such as liquid crystal on silicon (LCoS) display devices, which are sometimes referred to as light engines or projectors, operating as an example of a holographic projection system 538 within visualization device 213. In other words, visualization device 213 may include one or more see-through holographic lenses to present virtual images to a user. Hence, in some examples, visualization device 213 can operate to project 3D images onto the user's retinas via screen 520, e.g., formed by holographic lenses. In this manner, visualization device 213 may be configured to present a 3D virtual image to a user within a real-world view observed through screen 520, e.g., such that the virtual image appears to form part of the real-world environment. In some examples, visualization device 213 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Although the example of FIG. 4 illustrates visualization device 213 as a head-wearable device, visualization device 213 may have other forms and form factors. For instance, in some examples, visualization device 213 may be a handheld smartphone or tablet.

Visualization device 213 can also generate a user interface (UI) 522 that is visible to the user, e.g., as holographic imagery projected into see-through holographic lenses as described above. For example, UI 522 can include a variety of selectable widgets 524 that allow the user to interact with a mixed reality (MR) system, such as MR system 212 of FIG. 2. Imagery presented by visualization device 213 may include, for example, one or more 3D virtual objects. Details of an example of UI 522 are described elsewhere in this disclosure. Visualization device 213 also can include a speaker or other sensory devices 526 that may be positioned adjacent the user's ears. Sensory devices 526 can convey audible information or other perceptible information (e.g., vibrations) to assist the user of visualization device 213.

Visualization device 213 can also include a transceiver 528 to connect visualization device 213 to a processing device 510 and/or to network 208 and/or to a computing cloud, such as via a wired communication protocol or a wireless protocol, e.g., Wi-Fi, Bluetooth, etc. Visualization device 213 also includes a variety of sensors to collect sensor data, such as one or more optical camera(s) 530 (or other optical sensors) and one or more depth camera(s) 532 (or other depth sensors), mounted to, on or within frame 518. In some examples, the optical sensor(s) 530 are operable to scan the geometry of the physical environment in which user of MR system 212 is located (e.g., an operating room) and collect two-dimensional (2D) optical image data (either monochrome or color). Depth sensor(s) 532 are operable to provide 3D image data, such as by employing time of flight, stereo or other known or future-developed techniques for determining depth and thereby generating image data in three dimensions. Other sensors can include motion sensors 533 (e.g., Inertial Mass Unit (IMU) sensors, accelerometers, etc.) to assist with tracking movement.

MR system 212 processes the sensor data so that geometric, environmental, textural, etc. landmarks (e.g., corners, edges or other lines, walls, floors, objects) in the user's environment or "scene" can be defined and movements within the scene can be detected. As an example, the various types of sensor data can be combined or fused so that the user of visualization device 213 can perceive 3D images that can be positioned, or fixed and/or moved within the scene. When fixed in the scene, the user can walk around the 3D image, view the 3D image from different perspectives, and manipulate the 3D image within the scene using hand gestures, voice commands, gaze line (or direction) and/or other control inputs. As another example, the sensor data can be processed so that the user can position a 3D virtual object (e.g., a bone model) on an observed physical object in the scene (e.g., a surface, the patient's real bone, etc.) and/or orient the 3D virtual object with other virtual images displayed in the scene. As yet another example, the sensor data can be processed so that the user can position and fix a virtual representation of the surgical plan (or other widget, image or information) onto a surface, such as a wall of the operating room. Yet further, the sensor data can be used to recognize surgical instruments and the position and/or location of those instruments.

Visualization device 213 may include one or more processors 514 and memory 516, e.g., within frame 518 of the visualization device. In some examples, one or more external computing resources 536 process and store information, such as sensor data, instead of or in addition to in-frame processor(s) 514 and memory 516. In this way, data processing and storage may be performed by one or more processors 514 and memory 516 within visualization device 213 and/or some of the processing and storage requirements may be offloaded from visualization device 213. Hence, in some examples, one or more processors that control the operation of visualization device 213 may be within the visualization device, e.g., as processor(s) 514. Alternatively, in some examples, at least one of the processors that controls the operation of visualization device 213 may be external to the visualization device, e.g., as processor(s) 210. Likewise, operation of visualization device 213 may, in some examples, be controlled in part by a combination one or more processors 514 within the visualization device and one or more processors 210 external to the visualization device.

For instance, in some examples, when visualization device 213 is in the context of FIG. 2, processing of the sensor data can be performed by processing device(s) 210 in conjunction with memory or storage device(s) (M) 215. In some examples, processor(s) 514 and memory 516 mounted to frame 518 may provide sufficient computing resources to process the sensor data collected by cameras 530, 532 and motion sensors 533. In some examples, the sensor data can be processed using a Simultaneous Localization and Mapping (SLAM) algorithm, or other known or future-developed algorithm for processing and mapping 2D and 3D image data and tracking the position of visualization device 213 in the 3D scene. In some examples, image tracking may be performed using sensor processing and tracking functionality provided by the Microsoft HOLOLENS™ system, e.g., by one or more sensors and processors 514 within a visualization device 213 substantially conforming to the Microsoft HOLOLENS™ device or a similar mixed reality (MR) visualization device.

In some examples, MR system 212 can also include user-operated control device(s) 534 that allow the user to operate MR system 212, use MR system 212 in spectator mode (either as master or observer), interact with UI 522 and/or otherwise provide commands or requests to processing device(s) 210 or other systems connected to network 208. As examples, the control device(s) 234 can include a microphone, a touch pad, a control panel, a motion sensor or other types of control input devices with which the user can interact.

Figure 5:
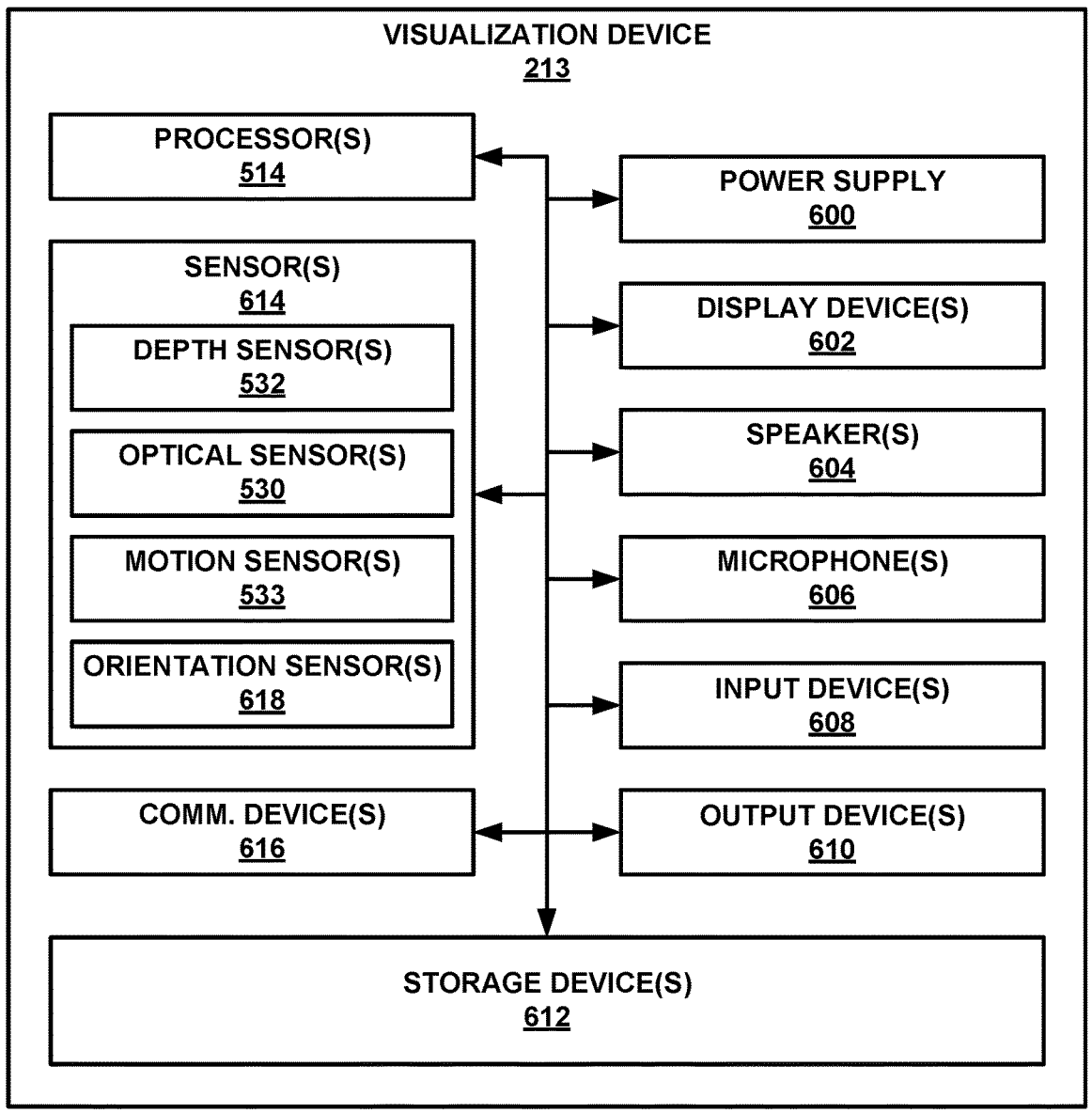
FIG. 5 is a block diagram illustrating example components of a visualization device for use in a mixed reality (MR) system, according to an example of this disclosure.

FIG. 5 is a block diagram illustrating example components of visualization device 213 for use in a MR system. In the example of FIG. 5, visualization device 213 includes processors 514, a power supply 600, display device(s) 602, speakers 604, microphone(s) 606, input device(s) 608, output device(s) 610, storage device(s) 612, sensor(s) 614, and communication devices 616. In the example of FIG. 5, sensor(s) 616 may include depth sensor(s) 532, optical sensor(s) 530, motion sensor(s) 533, and orientation sensor(s) 618. Optical sensor(s) 530 may include cameras, such as Red-Green-Blue (RGB) video cameras, infrared cameras, or other types of sensors that form images from light. Display device(s) 602 may display imagery to present a user interface to the user.

Speakers 604, in some examples, may form part of sensory devices 526 shown in FIG. 4. In some examples, display devices 602 may include screen 520 shown in FIG. 4. For example, as discussed with reference to FIG. 4, display device(s) 602 may include see-through holographic lenses, in combination with projectors, that permit a user to see real-world objects, in a real-world environment, through the lenses, and also see virtual 3D holographic imagery projected into the lenses and onto the user's retinas, e.g., by a holographic projection system. In this example, virtual 3D holographic objects may appear to be placed within the real-world environment. In some examples, display devices 602 include one or more display screens, such as LCD display screens, OLED display screens, and so on. The user interface may present virtual images of details of the virtual surgical plan for a particular patient.

In some examples, a user may interact with and control visualization device 213 in a variety of ways. For example, microphones 606, and associated speech recognition processing circuitry or software, may recognize voice commands spoken by the user and, in response, perform any of a variety of operations, such as selection, activation, or deactivation of various functions associated with surgical planning, intra-operative guidance, or the like. As another example, one or more cameras or other optical sensors 530 of sensors 614 may detect and interpret gestures to perform operations as described above. As a further example, sensors 614 may sense gaze direction and perform various operations as described elsewhere in this disclosure. In some examples, input devices 608 may receive manual input from a user, e.g., via a handheld controller including one or more buttons, a keypad, a touchscreen, joystick, trackball, and/or other manual input media, and perform, in response to the manual user input, various operations as described above.

As discussed above, surgical lifecycle 300 may include a preoperative phase 302 (FIG. 3). One or more users may use orthopedic surgical system 100 in preoperative phase 302. For instance, orthopedic surgical system 100 may include virtual planning system 102 to help the one or more users generate a virtual surgical plan that may be customized to an anatomy of interest of a particular patient. As described herein, the virtual surgical plan may include a 3-dimensional virtual model that corresponds to the anatomy of interest of the particular patient and a 3-dimensional model of one or more prosthetic components matched to the particular patient to repair the anatomy of interest or selected to repair the anatomy of interest. The virtual surgical plan also may include a 3-dimensional virtual model of guidance information to guide a surgeon in performing the surgical procedure, e.g., in preparing bone surfaces or tissue and placing implantable prosthetic hardware relative to such bone surfaces or tissue.

Figure 6:
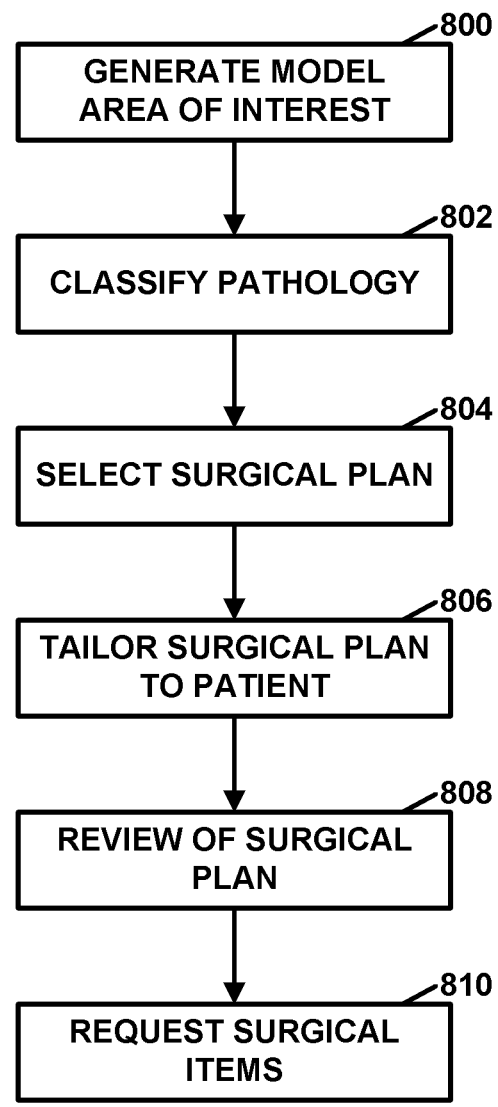
FIG. 6 is a flowchart illustrating example steps in the preoperative phase of the surgical lifecycle.

FIG. 6 is a flowchart illustrating example steps in preoperative phase 302 of surgical lifecycle 300. In other examples, preoperative phase 302 may include more, fewer, or different steps. Moreover, in other examples, one or more of the steps of FIG. 6 may be performed in different orders. In some examples, one or more of the steps may be performed automatically within a surgical planning system such as virtual planning system 102 (FIG. 1) or 202 (FIG. 2).

In the example of FIG. 6, a model of the area of interest is generated (800). For example, a scan (e.g., a CT scan, MRI scan, or other type of scan) of the area of interest may be performed. For example, if the area of interest is the patient's shoulder, a scan of the patient's shoulder may be performed. The virtual planning system may generate a virtual model (e.g., a three-dimensional virtual model) of the area of interest based on the scan. Furthermore, a pathology in the area of interest may be classified (802). In some examples, the pathology of the area of interest may be classified based on the scan of the area of interest. For example, if the area of interest is the user's shoulder, a surgeon may determine what is wrong with the patient's shoulder based on the scan of the patient's shoulder and provide a shoulder classification indicating the diagnosis, e.g., such as primary glenoid humeral osteoarthritis (PG-HOA), rotator cuff tear arthropathy (RCTA) instability, massive rotator cuff tear (MRCT), rheumatoid arthritis, post-traumatic arthritis, and osteoarthritis.

Additionally, a surgical plan may be selected based on the pathology (804). The surgical plan is a plan to address the pathology. For instance, in the example where the area of interest is the patient's shoulder, the surgical plan may be selected from an anatomical shoulder arthroplasty, a reverse shoulder arthroplasty, a post-trauma shoulder arthroplasty, or a revision to a previous shoulder arthroplasty. The surgical plan may then be tailored to patient (806). For instance, tailoring the surgical plan may involve selecting and/or sizing surgical items needed to perform the selected surgical plan. Additionally, the surgical plan may be tailored to the patient in order to address issues specific to the patient, such as the presence of osteophytes. As described in detail elsewhere in this disclosure, one or more users may use mixed reality systems of orthopedic surgical system 100 to tailor the surgical plan to the patient.

The surgical plan may then be reviewed (808). For instance, a consulting surgeon may review the surgical plan before the surgical plan is executed. As described in detail elsewhere in this disclosure, one or more users may use mixed reality (MR) systems of orthopedic surgical system 100 to review the surgical plan. In some examples, a surgeon may modify the surgical plan using an MR system by interacting with a UI and displayed elements, e.g., to select a different procedure, change the sizing, shape or positioning of implants, or change the angle, depth or amount of cutting or reaming of the bone surface to accommodate an implant.

Figure 7:
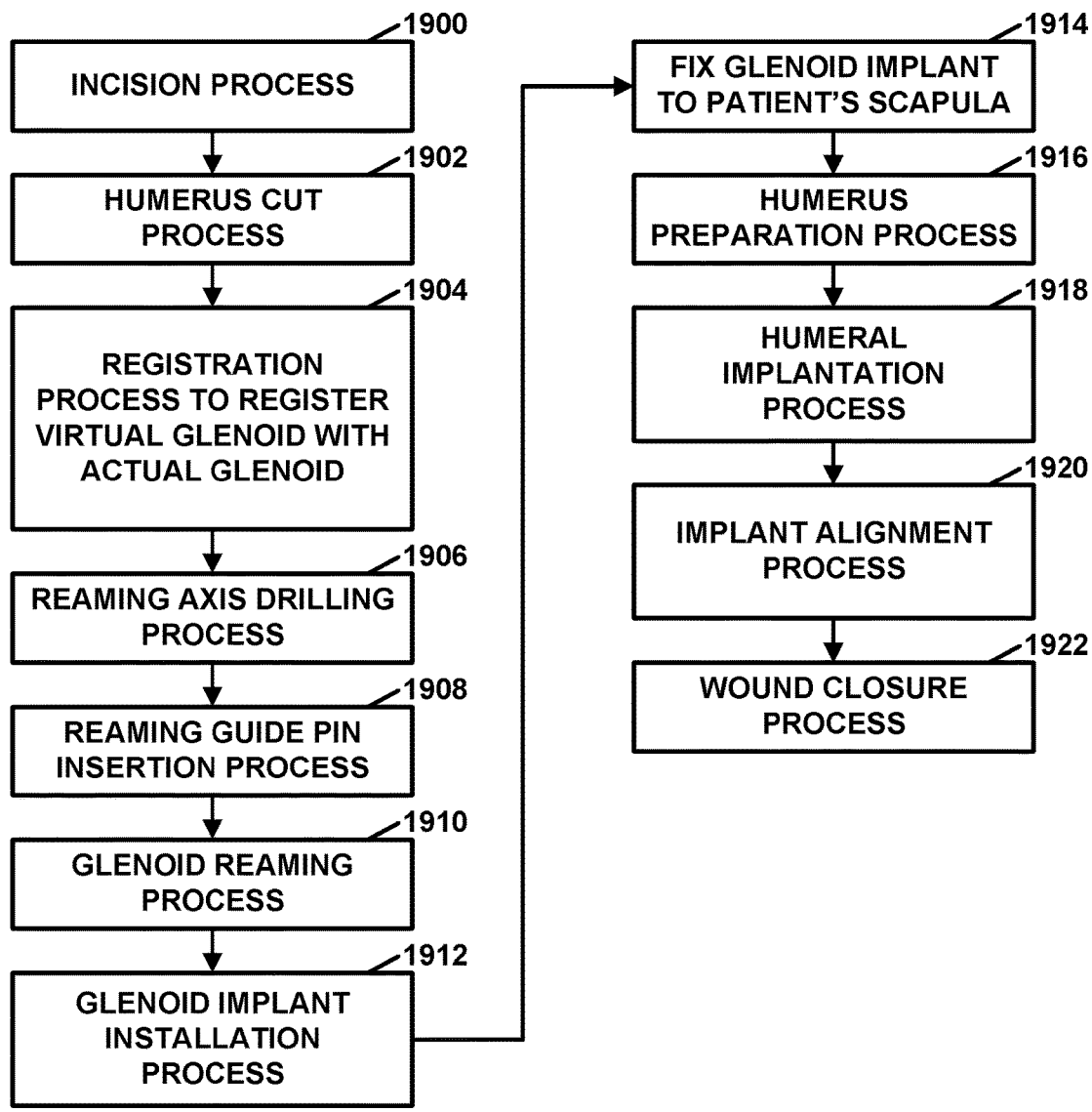
FIG. 7 is a flowchart illustrating example stages of a shoulder joint repair surgery.

FIG. 7 describes an example surgical process for a shoulder surgery that may use a registration marker with an anti-rotation based to register a virtual image to a physical space. The surgeon may wear or otherwise use visualization device 213 during each step of the surgical process. In other examples, a shoulder surgery may include more, fewer, or different steps. For example, a shoulder surgery may include step for adding a bone graft, adding cement, and/or other steps. In some examples, visualization device 213 may present virtual guidance to guide the surgeon, nurse, or other users, through the steps in the surgical workflow.

In the example of FIG. 7, a surgeon performs an incision process (1900). During the incision process, the surgeon makes a series of incisions to expose a patient's shoulder joint. In some examples, an MR system (e.g., MR system 212, MR system 1800A, etc.) may help the surgeon perform the incision process, e.g., by displaying virtual guidance imagery illustrating how to where to make the incision.

Furthermore, in the example of FIG. 7, the surgeon may perform a humerus cut process (1902). During the humerus cut process, the surgeon may remove a portion of the humeral head of the patient's humerus. Removing the portion of the humeral head may allow the surgeon to access the patient's glenoid. Additionally, removing the portion of the humeral head may allow the surgeon to subsequently replace the portion of the humeral head with a humeral implant compatible with a glenoid implant that the surgeon plans to implant in the patient's glenoid.

As discussed above, the humerus preparation process may enable the surgeon to access the patient's glenoid. In the example of FIG. 7, after performing the humerus preparation process, the surgeon may perform a registration process that registers a virtual glenoid object with the patient's actual glenoid bone (1904) in the field of view presented to the surgeon by visualization device 213.

Figure 8:
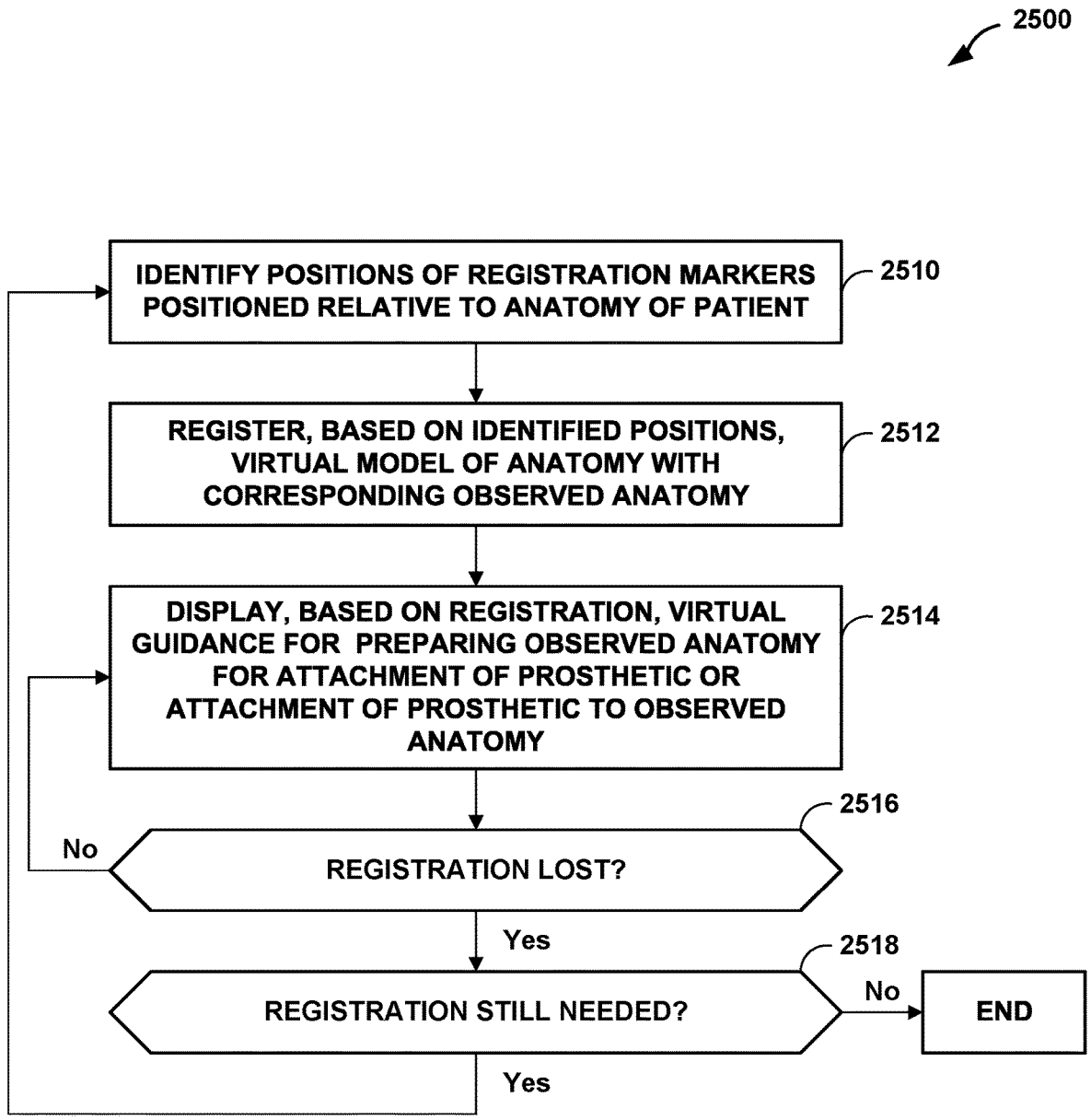
FIG. 8 illustrates an example technique for registering a 3-dimensional virtual bone model with an observed real bone structure of a patient during joint repair surgery.

FIG. 8 illustrates an example of a technique 2500 for registering a 3D virtual bone model with a real observed bone structure of a patient using physical markers (e.g., any combination of passive and active physical markers). In other words, FIG. 8 is an example of a process flow, e.g., performed by visualization device 213, for registering a virtual bone model with an observed bone that is implemented in a mixed reality system, such as the mixed reality system 212 of FIG. 2. 3D virtual bone model may be a model of all or part of one or more bones. The process flow of FIG. 8 may be performed as part of the registration process of step 1904 of FIG. 7.

In operation, the practitioner may place one or more physical markers at specific positions (e.g., the registration marker 900 of FIGS. 9, 11A, and 11B below). In some examples, MR system 212 may output instructions as to where the practitioner should place the physical markers. For example, a physical marker may be placed such that it rests on and bears against a surface of a superior of the glenoid. The prescribed locations may correspond to specific locations on a virtual model that corresponds to the observed bone structure.

MR system 212 may utilize data from one or more sensors (e.g., one or more of sensors 614 of visualization device 213 of FIG. 5) to identify the location of the registration marker(s) (e.g., the registration marker 900 of FIGS. 9, 11A and 11B below) (2510). For instance, MR system 212 may use data generated by any combination of depth sensors 532 and/or optical sensors 530 to identify a specific position (e.g., coordinates) the registration marker(s). As one specific example, MR system 212 may utilize optical data generated by optical sensors 530 to identify a centroid of the registration marker. MR system 212 may then utilize depth data generated by depth sensors 532 and/or optical data generated by optical sensors 530 to determine a position and/or orientation of the identified centroid. MR system 212 may determine a distance between the centroid and an attachment point of the registration marker. Based on the determined distance (i.e., between the centroid and the attachment point) and the determined position/orientation of the centroid, MR system 212 may determine a position/orientation of the attachment point.

MR system 212 may register the virtual model with the observed anatomy based on the identified positions (2512) of the registration marker(s). For instance, where the registration marker(s) is/are placed on the observed bone structure at locations that correspond to specific location(s) on the virtual model that corresponds to the observed bone structure, MR system 212 may generate a transformation matrix between the virtual model and the observed bone structure 212. This transformation matrix may allow for translation along the x, y, and z axes of the virtual model and rotation about the x, y and z axes in order to achieve and maintain alignment between the virtual and observed bones. In some examples, after registration is complete, MR system 212 utilize the results of the registration to perform simultaneous localization and mapping (SLAM) to maintain alignment of the virtual model to the corresponding observed object.

In some examples, the practitioner may remove the physical markers (e.g., after registration is complete). For instance, after MR system 212 has completed the registration process using the physical markers, MR system 212 may output an indication that the physical markers may be removed. In example where the physical markers are removed, MR system 212 may subsequently maintain the registration of the virtual bone model to the observed bone using virtual markers or any other suitable tracking technique.

In some examples, the practitioner may not remove the physical markers until a later point in the surgery. For instance, the practitioner may not remove the physical markers until registration of the virtual model to the observed bone is no longer required (e.g., after all virtual guidance that uses the registration has been displayed and corresponding surgical steps have been completed).

In some examples, MR system 212 may be able to maintain the registration between a virtual bone model and observed bone (e.g., glenoid, humerus, or other bone structure) throughout the procedure. However, in some cases, MR system 212 may lose, or otherwise be unable to maintain, the registration between the virtual bone model and observed bone. For instance, MR system 212 may lose track of the registration marker(s). This loss may be the result of any number of factors including, but not limited to, body fluids (e.g., blood) occluding the markers, the markers becoming dislodged (e.g., a physical marker being knocked out of position), and the like. As such, MR system 212 may periodically determine whether registration has been lost (2516).

In some examples, MR system 212 may determine that registration has been lost where a confidence distance between a virtual point and a corresponding physical point exceeds a threshold confidence distance (e.g., a clinical value). MR system 212 may periodically determine the confidence distance as a value that represents the accuracy of the current registration. For instance, MR system 212 may determine that a distance between a virtual point and a corresponding physical point is less than 3 mm.

In some examples, MR system 212 may output a representation of the confidence distance. As one example, MR system 212 may cause visualization device 213 to display a numerical value of the confidence distance. As another example, MR system 212 may cause visualization device 213 to display a graphical representation of the confidence distance relative to the threshold confidence distance (e.g., display a green circle if the confidence distance is less than half of the threshold confidence distance, display a yellow circle if the confidence distance is between half of the threshold confidence distance and the threshold confidence distance, and display a red circle if the confidence distance greater than the threshold confidence distance).

In some examples, MR system 212 may utilize the same threshold confidence distance throughout a surgical procedure. In some examples, MR system 212 may utilize different threshold confidence distances for various parts a surgical procedure. For instance, MR system 212 may utilize a first threshold confidence distance for a first set of work steps and use a second threshold confidence distance (that is different than the first threshold confidence distance) for a first set of work steps for a second set of work steps.

Where registration has not been lost ("No" branch of 2516), MR system 212 may continue to display virtual guidance (2514). However, where MR system 212 loses registration ("Yes" branch of 2516), MR system 212 may perform one or more actions to re-register the virtual bone model to the observed bone. As one example, MR system 212 may automatically attempt to perform the registration process without further action from the practitioner. For instance, where physical markers have not been removed. MR system 212 may perform the registration process using the physical markers. Alternatively, where the physical markers have been removed (or were never placed), MR system 212 may output a request for the practitioner to place the physical markers. As such, MR system 212 may be considered to periodically register the virtual model with the observed bone.

In some examples, as opposed to automatically attempting re-registration where registration is lost, MR system 212 may selectively perform re-registration based on whether registration is still needed (2518). In some examples, MR system 212 may determine that registration is still needed if additional virtual guidance will be displayed. Where MR system 212 determines that registration is no longer needed ("No" branch of 2518), MR system 212 may end the registration procedure.

As described above, MR system 212 may utilize any combination of virtual and physical markers to enable registration of virtual models to corresponding observed structures. MR system 212 may use any of the markers to perform an initial registration and, where needed, MR system 212 may use any of the markers to perform a re-registration. The markers used for the initial registration may be the same as or may be different than the markers used for any re-registrations.

In some examples, to enhance the accuracy and quality of registration, during the initialization stage of the registration process, MR system 212 can compute and display spatial constraints for user head pose and orientation. These constraints can be computed in real time and depend on the position of the user, and/or the orientation, and/or the distance to the observed bone, and/or the depth camera characteristics. For example, MR system 212 may prompt the user to move closer to the observed bone, to adjust the head position so that the user's gaze line is perpendicular to the surface of interest of the observed bone, or to make any other adjustments that can be useful to enhance the registration process and which may depend on the particular surgical application and/or the attributes of the particular anatomy of interest and/or the characteristics of the optical and depth sensors that are employed in MR system 212.

In some examples, depth camera(s) 532 detect distance by using a structured light approach or time of flight of an optical signal having a suitable wavelength. In general, the wavelength of the optical signal is selected so that penetration of the surface of the observed anatomy by the optical signal transmitted by depth camera(s) 532 is minimized. It should be understood, however, that other known or future developed techniques for detecting distance also can be employed.

As discussed below, the registration techniques described herein may be performed for any pair of virtual model and observed object. As one example, an MR system may utilize the registration techniques to register a virtual model of a bone to an observed bone. As another example, an MR system may utilize the registration techniques to register a virtual model of an implant to an observed implant. An MR system may utilize the registration techniques to register a virtual model of a tool to an observed tool.

In some examples, an MR system may perform the registration techniques once for a particular pair of a virtual model and an observed object (e.g., within a particular surgical procedure). For instance, an MR system may register a virtual model of a glenoid with an observed glenoid and utilize the registration to provide virtual guidance for multiple steps of a surgical procedure. In some examples, an MR system may perform the registration techniques multiple times for a particular pair of a virtual model and an observed object (e.g., within a particular surgical procedure). For instance, an MR system may first register a virtual model of a glenoid with an observed glenoid and utilize the registration to provide virtual guidance for one or more steps of a surgical procedure. Then, for example, after material has been removed from the glenoid (e.g., via reaming), the MR system may register another virtual model of the glenoid (that accounts for the removed material) with an observed glenoid and use the subsequent registration to provide virtual guidance for one or more other steps of the surgical procedure.

The registration process may be used in conjunction with the virtual planning processes and/or intra-operative guidance described elsewhere in this disclosure. Thus, in one example, a virtual surgical plan is generated or otherwise obtained to repair an anatomy of interest of a particular patient (e.g., the shoulder joint of the particular patient). In instances where the virtual surgical plan is obtained, another computing system may generate the virtual surgical plan and an MR system (e.g., MR system 212) or other computing system obtains the virtual surgical plan from a computer readable medium, such as a communication medium or a non-transitory storage medium. In this example, the virtual surgical plan may include a 3D virtual model of the anatomy of interest generated based on preoperative image data and a prosthetic component selected for the particular patient to repair the anatomy of interest. Furthermore, in this example, a user may use a MR system (e.g., MR system 212) to implement the virtual surgical plan. In this example, as part of using the MR system, the user may request the virtual surgical plan for the particular patient.

Additionally, the user may view virtual images of the surgical plan projected within a real environment. For example, MR system 212 may present 3D virtual objects such that the objects appear to reside within a real environment, e.g., with real anatomy of a patient, as described in various examples of this disclosure. In this example, the virtual images of the surgical plan may include one or more of the 3D virtual model of the anatomy of interest, a 3D model of the prosthetic component, and virtual images of a surgical workflow to repair the anatomy of interest. Furthermore, in this example, the user may register the 3D virtual model with a real anatomy of interest of the particular patient. The user may then implement the virtually generated surgical plan to repair the real anatomy of interest based on the registration. In other words, in the augmented surgery mode, the user can use the visualization device to align the 3D virtual model of the anatomy of interest with the real anatomy of interest.

In some examples, as part of registering the 3D virtual model with the real anatomy of interest, the 3D virtual model can be aligned (e.g., by the user) with the real anatomy of interest and generate a transformation matrix between the 3D virtual model and the real anatomy of interest based on the alignment. The transformation matrix provides a coordinate system for translating the virtually generated surgical plan to the real anatomy of interest. For instance, the registration process may allow the user to view steps of the virtual surgical plan projected on the real anatomy of interest. For instance, the alignment of the 3D virtual model with the real anatomy of interest may generate a transformation matrix that may allow the user to view steps of the virtual surgical plan (e.g., identification of an entry point for positioning a prosthetic implant to repair the real anatomy of interest) projected on the real anatomy of interest.

With continued reference to FIG. 7, after performing the registration process, the surgeon may perform a reaming axis drilling process (1906). During the reaming axis drilling process, the surgeon may drill a reaming axis guide pin hole in the patient's glenoid to receive a reaming guide pin. At a later stage of the shoulder surgery, the surgeon may insert a reaming axis pin into the reaming axis guide pin hole. In some examples, an MR system (e.g., MR system 212, MR system 1800A, etc.) may present a virtual reaming axis to help the surgeon perform the drilling in alignment with the reaming axis and thereby place the reaming guide pin in the correct location and with the correct orientation.

The surgeon may perform the reaming axis drilling process in one of various ways. For example, the surgeon may perform a guide-based process to drill the reaming axis pin hole. In the case, a physical guide is placed on the glenoid to guide drilling of the reaming axis pin hole. In other examples, the surgeon may perform a guide-free process, e.g., with presentation of a virtual reaming axis that guides the surgeon to drill the reaming axis pin hole with proper alignment. An MR system (e.g., MR system 212, MR system 1800A, etc.) may help the surgeon perform either of these processes to drill the reaming axis pin hole.

Furthermore, in the surgical process of FIG. 7, the surgeon may perform a reaming axis pin insertion process (1908). During the reaming axis pin insertion process, the surgeon inserts a reaming axis pin into the reaming axis pin hole drilled into the patient's scapula. In some examples, an MR system (e.g., MR system 212, MR system 1800A, etc.) may present virtual guidance information to help the surgeon perform the reaming axis pin insertion process.

After performing the reaming axis insertion process, the surgeon may perform a glenoid reaming process (1910). During the glenoid reaming process, the surgeon reams the patient's glenoid. Reaming the patient's glenoid may result in an appropriate surface for installation of a glenoid implant. In some examples, to ream the patient's glenoid, the surgeon may affix a reaming bit to a surgical drill. The reaming bit defines an axial cavity along an axis of rotation of the reaming bit. The axial cavity has an inner diameter corresponding to an outer diameter of the reaming axis pin. After affixing the reaming bit to the surgical drill, the surgeon may position the reaming bit so that the reaming axis pin is in the axial cavity of the reaming bit. Thus, during the glenoid reaming process, the reaming bit may spin around the reaming axis pin. In this way, the reaming axis pin may prevent the reaming bit from wandering during the glenoid reaming process. In some examples, multiple tools may be used to ream the patient's glenoid. An MR system (e.g., MR system 212, MR system 1800A, etc.) may present virtual guidance to help the surgeon or other users to perform the glenoid reaming process. For example, the MR system may help a user, such as the surgeon, select a reaming bit to use in the glenoid reaming process. In some examples, the MR system present virtual guidance to help the surgeon control the depth to which the surgeon reams the user's glenoid. In some examples, the glenoid reaming process includes a paleo reaming step and a neo reaming step to ream different parts of the patient's glenoid.

Additionally, in the surgical process of FIG. 7, the surgeon may perform a glenoid implant installation process (1912). During the glenoid implant installation process, the surgeon installs a glenoid implant in the patient's glenoid. In some instances, when the surgeon is performing an anatomical shoulder arthroplasty, the glenoid implant has a concave surface that acts as a replacement for the user's natural glenoid. In other instances, when the surgeon is performing a reverse shoulder arthroplasty, the glenoid implant has a convex surface that acts as a replacement for the user's natural humeral head. In this reverse shoulder arthroplasty, the surgeon may install a humeral implant that has a concave surface that slides over the convex surface of the glenoid implant. As in the other steps of the shoulder surgery of FIG. 7, an MR system (e.g., MR system 212, MR system 1800A, etc.) may present virtual guidance to help the surgeon perform the glenoid installation process.

In some examples, the glenoid implantation process includes a process to fix the glenoid implant to the patient's scapula (1914). In some examples, the process to fix the glenoid implant to the patient's scapula includes drilling one or more anchor holes or one or more screw holes into the patient's scapula and positioning an anchor such as one or more pegs or a keel of the implant in the anchor hole(s) and/or inserting screws through the glenoid implant and the screw holes, possibly with the use of cement or other adhesive. An MR system (e.g., MR system 212, MR system 1800A, etc.) may present virtual guidance to help the surgeon with the process of fixing the glenoid implant the glenoid bone, e.g., including virtual guidance indicating anchor or screw holes to be drilled or otherwise formed in the glenoid, and the placement of anchors or screws in the holes.

Furthermore, in the example of FIG. 7, the surgeon may perform a humerus preparation process (1916). During the humerus preparation process, the surgeon prepares the humerus for the installation of a humerus implant. In instances where the surgeon is performing an anatomical shoulder arthroplasty, the humerus implant may have a convex surface that acts as a replacement for the patient's natural humeral head. The convex surface of the humerus implant slides within the concave surface of the glenoid implant. In instances where the surgeon is performing a reverse shoulder arthroplasty, the humerus implant may have a concave surface and the glenoid implant has a corresponding convex surface. As described elsewhere in this disclosure, an MR system (e.g., MR system 212, MR system 1800A, etc.) may present virtual guidance information to help the surgeon perform the humerus preparation process.

Furthermore, in the example surgical process of FIG. 7, the surgeon may perform a humerus implant installation process (1918). During the humerus implant installation process, the surgeon installs a humerus implant on the patient's humerus. As described elsewhere in this disclosure, an MR system (e.g., MR system 212, etc.) may present virtual guidance to help the surgeon perform the humerus preparation process.

After performing the humerus implant installation process, the surgeon may perform an implant alignment process that aligns the installed glenoid implant and the installed humerus implant (1920). For example, in instances where the surgeon is performing an anatomical shoulder arthroplasty, the surgeon may nest the convex surface of the humerus implant into the concave surface of the glenoid implant. In instances where the surgeon is performing a reverse shoulder arthroplasty, the surgeon may nest the convex surface of the glenoid implant into the concave surface of the humerus implant. Subsequently, the surgeon may perform a wound closure process (1922). During the wound closure process, the surgeon may reconnect tissues severed during the incision process in order to close the wound in the patient's shoulder.

For a shoulder arthroplasty application, the registration process may start by virtualization device 213 presenting the user with 3D virtual bone model of the patient's scapula and glenoid that was generated from preoperative images of the patient's anatomy, e.g., by surgical planning system 102. The user can then manipulate 3D virtual bone model in a manner that aligns and orients 3D virtual bone model with the patient's real scapula and glenoid that the user is observing in the operating environment. As such, in some examples, the MR system may receive user input to aid in the initialization and/or registration. However, discussed above, in some examples, the MR system may perform the initialization and/or registration process automatically (e.g., without receiving user input to position the 3D bone model).

For other types of arthroplasty procedures, such as for the knee, hip, foot, ankle or elbow, different relevant bone structures can be displayed as virtual 3D images and aligned and oriented in a similar manner with the patient's actual, real anatomy.

Regardless of the particular type of joint or anatomical structure involved, selection of the augment surgery mode initiates a procedure where 3D virtual bone model is registered with an observed bone structure. In general, the registration procedure can be considered as a classical optimization problem (e.g., either minimization or maximization). For a shoulder arthroplasty procedure, known inputs to the optimization (e.g., minimization) analysis are the 3D geometry of the observed patient's bone (derived from sensor data from the visualization device 213, including depth data from the depth camera(s) 532) and the geometry of the 3D virtual bone derived during the virtual surgical planning state (such as by using the BLUEPRINT™ system). Other inputs include details of the surgical plan (also derived during the virtual surgical planning stage, such as by using the BLUEPRINT™ system), such as the position and orientation of entry points, cutting planes, reaming axes and/or drilling axes, as well as reaming or drilling depths for shaping the bone structure, the type, size and shape of the prosthetic components, and the position and orientation at which the prosthetic components will be placed or, in the case of a fracture, the manner in which the bone structure will be rebuilt.

Upon selection of a particular patient from a welcome page of UI presented by MR system 212 (FIG. 4), the surgical planning parameters associated with that patient are connected with the patient's 3D virtual bone model, e.g., by one or more processors of visualization device 213. In the Augment Surgery mode, registration of 3D virtual bone model (with the connected preplanning parameters) with the observed bone by visualization device 213 allows the surgeon to visualize virtual representations of the surgical planning parameters on the patient.

The optimization (e.g., minimization) analysis that is implemented to achieve registration of the 3D virtual bone model with the real bone generally is performed in two stages: an initialization stage and an optimization (e.g., minimization) stage. During the initialization stage, the user approximately aligns the 3D virtual bone model with the patient's real bone, such as by using gaze direction, hand gestures and/or voice commands to position and orient, or otherwise adjust, the alignment of the virtual bone with the observed real bone. The initialization stage will be described in further detail below. During the optimization (e.g., minimization) stage, which also will be described in detail below, an optimization (e.g., minimization) algorithm is executed that uses information from the optical camera(s) 530 and/or depth camera(s) 532 and/or any other acquisition sensor (e.g., motion sensors 533) to further improve the alignment of the 3D model with the observed anatomy of interest. In some examples, the optimization (e.g., minimization) algorithm can be a minimization algorithm, including any known or future-developed minimization algorithm, such as an Iterative Closest Point algorithm or a genetic algorithm as examples.

In this way, in one example, a mixed reality surgical planning method includes generating a virtual surgical plan to repair an anatomy of interest of a particular patient. The virtual surgical plan including a 3D virtual model of the anatomy of interest is generated based on preoperative image data and a prosthetic component selected for the particular patient to repair the anatomy of interest. Furthermore, in this example, the method includes using a MR visualization system to implement the virtual surgical plan. In this example, using the MR system may comprise requesting the virtual surgical plan for the particular patient. Using the MR system also comprises viewing virtual images of the surgical plan projected within a real environment. For example, visualization device 213 may be configured to present one or more 3D virtual images of details of the surgical plan that are projected within a real environment, e.g., such that the virtual image(s) appear to form part of the real environment. The virtual images of the surgical plan may include the 3D virtual model of the anatomy of interest, a 3D model of the prosthetic component, and virtual images of a surgical workflow to repair the anatomy of interest. Using the MR system may also include registering the 3D virtual model with a real anatomy of interest of the particular patient. Additionally, in this example, using the MR system may include implementing the virtually generated surgical plan to repair the real anatomy of interest based on the registration.

Furthermore, in some examples, the method comprises registering the 3D virtual model with the real anatomy of interest without using virtual or physical markers. The method may also comprise using the registration to track movement of the real anatomy of interest during implementation of the virtual surgical plan on the real anatomy of interest. The movement of the real anatomy of interest may be tracked without the use of tracking markers. In some instances, registering the 3D virtual model with the real anatomy of interest may comprise aligning the 3D virtual model with the real anatomy of interest and generating a transformation matrix between the 3D virtual model and the real anatomy of interest based on the alignment. The transformation matrix provides a coordinate system for translating the virtually generated surgical plan to the real anatomy of interest. In some examples, aligning may comprise virtually positioning a point of interest on a surface of the 3D virtual model within a corresponding region of interest on a surface of the real anatomy of interest; and adjusting an orientation of the 3D virtual model so that a virtual surface shape associated with the point of interest is aligned with a real surface shape associated with the corresponding region of interest. In some examples, aligning may further comprise rotating the 3D virtual model about a gaze line of the user. The region of interest may be an anatomical landmark of the anatomy of interest. The anatomy of interest may be a shoulder joint. In some examples, the anatomical landmark is a center region of a glenoid.

In some examples, after a registration process is complete, a tracking process can be initiated that continuously and automatically verifies the registration between 3D virtual bone model and observed bone structure during the Augment Surgery mode. During a surgery, many events can occur (e.g., patient movement, instrument movement, loss of tracking, etc.) that may disturb the registration between the 3D anatomical model and the corresponding observed patient anatomy or that may impede the ability of MR system 212 to maintain registration between the model and the observed anatomy. Therefore, by implementing a tracking feature, MR system 212 can continuously or periodically verify the registration and adjust the registration parameters as needed. If MR system 212 detects an inappropriate registration (such as patient movement that exceeds a threshold amount), the user may be asked to re-initiate the registration process.

As discussed above, MR system 212 initially registers the 3D virtual bone model with the observed bone structure using a registration marker. MR system 212 may continue to track a position of the registration marker and utilize said tracked position to guide surgical steps. For instance, MR system 212 may output, for display, a virtual axis at a position relative to the position of the registration marker. As such, if the registration marker is rotated or otherwise moved during the procedure, the surgical steps guided by MR system 212 based on the position of the registration marker may be performed with reduced accuracy. For example, if the registration marker is jostled or bumped into, causing it to rotate, during the procedure, MR system 212 may display the virtual axis at an incorrect location on the bone, even though the virtual axis is still displayed at the correct relative position to the registration marker. As such, maintaining a non-rotating, fixed reference facilitates providing a stable alignment with minimal interruption to the procedure may be desirable.

In accordance with one or more aspects of this disclosure, a registration marker may be attached to bone via an anti-rotation base. For instance, as discussed in further detail below, the anti-rotation base may include a plurality of pin receptacles that each define a respective pin axis. At least two of the pin axes may not be parallel. As such, when pins are installed via the pin receptacles, the anti-rotation base will be secured to the bone via at least two non-parallel pins. By virtue of having non-parallel pins, the anti-rotation base may better resist rotation (e.g., as compared to pins that are parallel). In this way, the registration marker may be more securely attached to bone, which may improve the accuracy of surgical steps guided based on a position of the registration marker.

Figure 9:
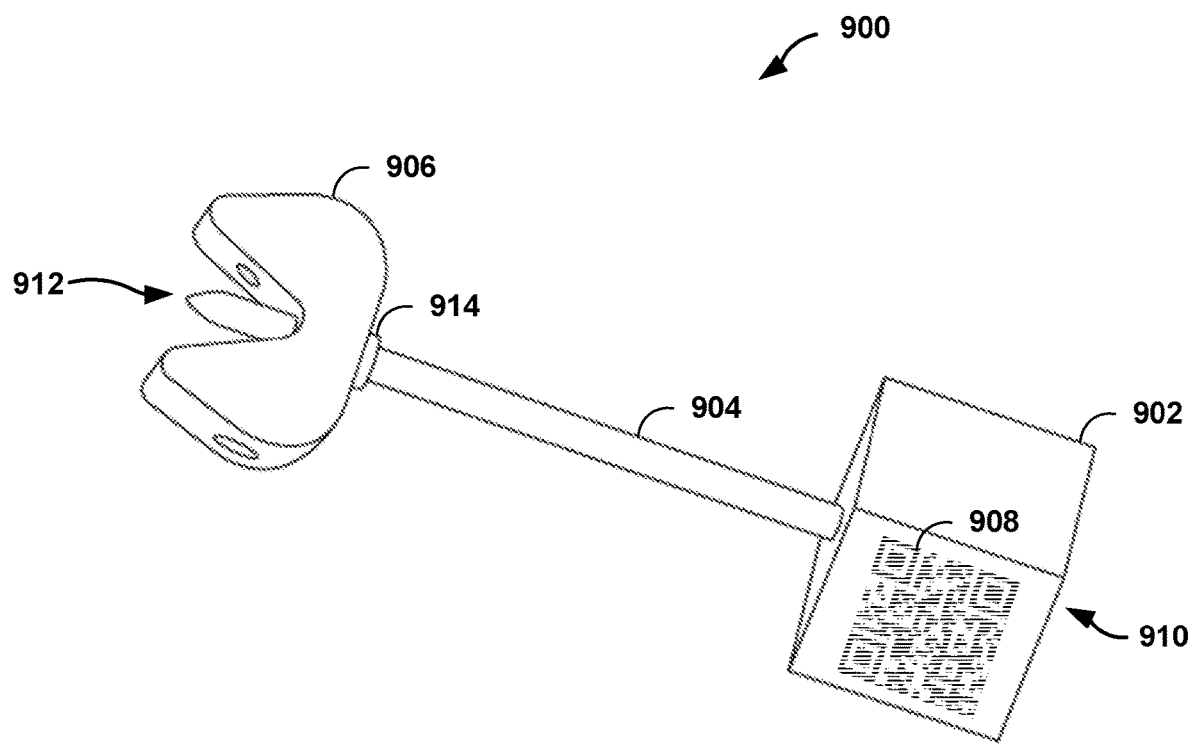
FIG. 9 illustrates an example registration marker with an anti-rotation base.
Figure 10A:
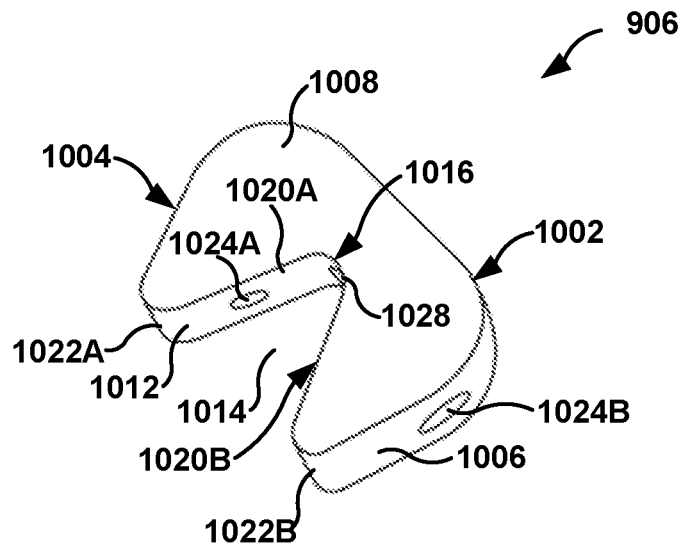
FIG. 10A is a perspective view of an example anti-rotation base.
Figure 10B:
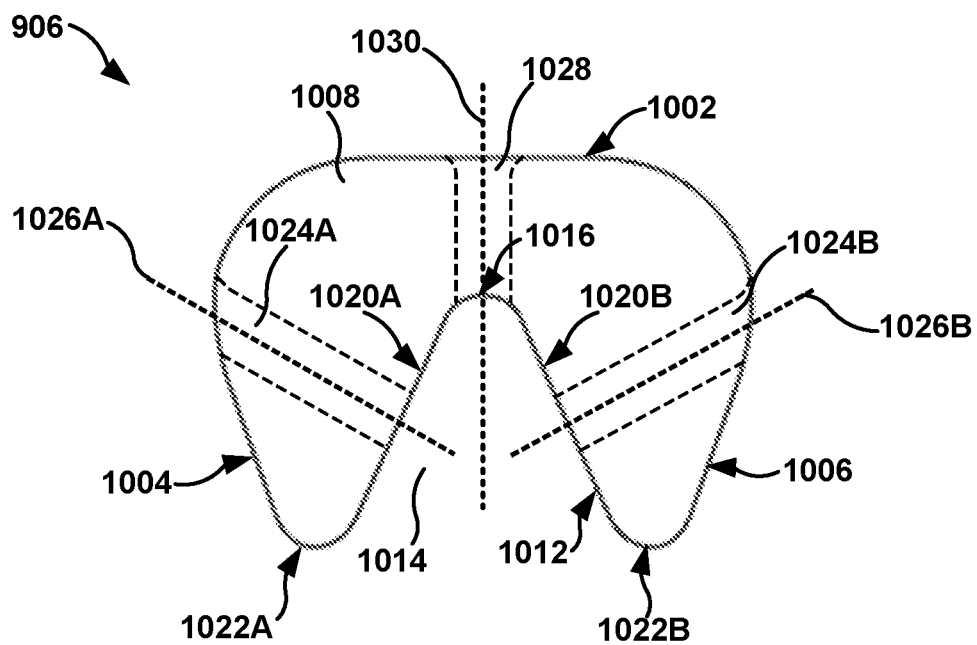
FIG. 10B is a front view of an example anti-rotation base.
Figure 10C:
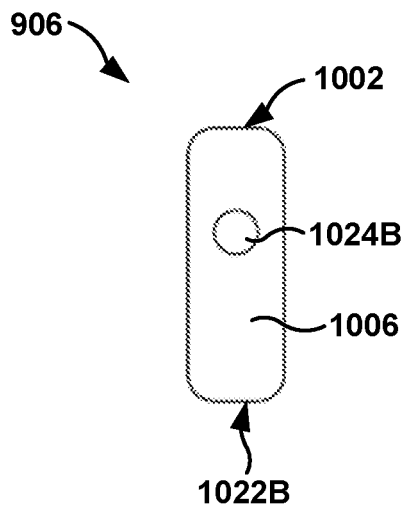
FIG. 10C is a right view of an example anti-rotation base.
Figure 10D:
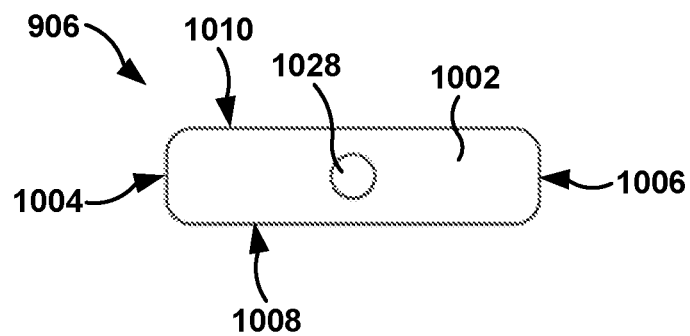
FIG. 10D is a top view of an example anti-rotation base.
Figure 10E:
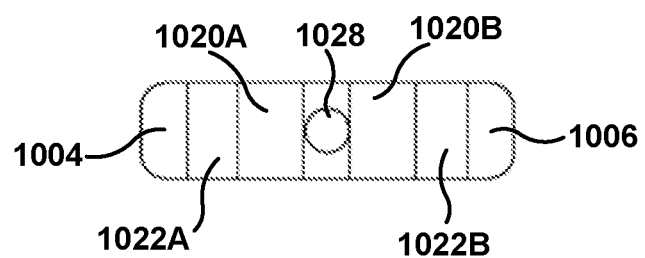
FIG. 10E is a bottom view of an example anti-rotation base.

FIG. 9 illustrates an example registration marker 900. In the illustrated example, registration marker 900 include a fiducial marker 902, a mounting rod 904, and an anti-rotation based 906. Registration marker 900, when installed, may rest on and bear against surface of the bone (e.g., a superior region of glenoid, etc.) with fiducial marker 902 is spaced away from the surface of the patient to provide a reference to align a virtual object with its corresponding physical object (e.g., to align a virtual representation of a glenoid in an MR system to the physical location of the patient's glenoid, etc.).

Fiducial marker 902 includes indicia 908 one or more sides to facilitate locating a centroid of registration marker 900 and/or an orientation of registration marker 900 in space. In the illustrated example, fiducial marker 902 is a polyhedron with indicia 908 on multiple sides (e.g., three sides, etc.) to facilitate an MR system establishing relative three-dimensional axes (e.g., an x-axis, a y-axis, and a z-axis). Indicia 908 are markings that are readable by a computer vision system that are, in some examples, decodable (e.g., QR codes, bar codes, images, etc.) to facilitate determining the orientation and location of fiducial marker 902. In some examples, one or more of indicia 908 may include markings that indicate aspects about their location on fiducial marker 902. As one example, an indicia of indicia 908 may encode an indication that it is on a front face of fiducial marker 902. As another example, an indicia of indicia 908 may encode an indication that it is on a top face of fiducial marker 902.

Mounting rod 904 includes a proximal end 910 and a distal end 912. Fiducial marker 902 is affixed or to integrated into the distal end 912. The proximal end 910 is configured to be slidably mountable to anti-rotation abase 906. In the illustrate example, mounting rod 904 includes a flange portion 914 configured to limit a range in which anti-rotation base 906 slides about mounting rod 904. In some example, the distal end 912 is configured to be anchored to a bone of the patient.

As described below in FIGS. 10A-10E, anti-rotation based 906 is configured to straddle a bone of the patient to resist rotation of registration marker 900. The anti-rotation based 906 is defined by a top surface 1002, side surfaces 1004 and 1006, a front surface 1008, a back surface 1010, and a bottom surface 1012. In the illustrated example, front surface 1008 and back surface 1010 are parallel. In some examples, front surface 1008 and back surface 1010 are flat.

In the illustrated example, bottom surface 1012 is curved to define a cavity 1014. When installed in a patient, at least a portion of a bone of the patient is within cavity 1014. In some examples, bottom surface 1012 rests on and bear against a surface a glenoid of the patient such that a portion of the glenoid is within cavity 1014. For example, when installed, cavity 1014 may straddle a superior region of the glenoid. In some examples, cavity 1014 is parabolic. In some examples, a shape of cavity 1014 is tailored to a shape of a bone of a particular patient that anti-rotation based 906 is to straddle based on, for example, images and/or models of the bone. In some examples, the shape of cavity 1014 may have predefine variations, where the particular shape of cavity 1014 of a particular patient is selected based on pre-operative images of the patient. In the illustrated examples, the curve of bottom surface 1004 has an apex 1016 that defines a narrow portion of anti-rotation based 906. Apex 1016 also defines two sides 1020A and 1020B of bottom surface 1012. In some examples, when anti-rotation base 906 is tailored to a shape of the bone of a particular patient, sides 1020A and 1020B may be modified. In some examples, anti-rotation base 906 may be pre-manufactured in different sizes and/or shapes. In some such examples, different ones of anti-rotation bases 906 may be manufactured such that sides 1020A and 1020B have different sizes and shapes. For example, a slope and/or curvature of one or more of sides 1020A and 1020B may be changed and/or a length of one or more of sides 1020A and 1020B may be elongated or shortened. While in the illustrated example, cavity 1014 is an arch, cavity 1014 may be any shape that facilitates anti-rotation base 906 straddling a bone of a patient. In the illustrated examples, side 1020A of bottom surface 112 meets side surface 1004 at an apex 1022A and side 1020B of bottom surface 112 meets side surface 1006 at an apex 1022B.

Anti-rotation base 906 defines a plurality of pin receptacles 1024A and 1024B (collectively "pin receptacles 1024") around respective pin axes 1026A and 1026B. In the illustrated example, a first pin receptacle 1024A extends from side surface 1004 through anti-rotation base 906 and a second pin receptacle 1022A extends from side surface 1006 through anti-rotation base 906. Pin axes 1026A and 1026B are not parallel and are configured that when anti-rotation based 906 is installed in the patient, pins (e.g., the pins 1102 of FIGS. 11 and 12 below) that are embedded into the bone do not interfere with each other (e.g., the pin axes do not intersect). For example, one pin receptacle 1024A may be offset from the other pin receptacle 1024B. In the illustrated example, anti-rotation base 906 defines two pin receptacles 1024A and 1024B. However, anti-rotation base 906 may have more or fewer pin receptacles. For instance, anti-rotation base 906 may include three, four, or more pin receptacles.

In the illustrated examples, anti-rotation base 906 defines a mounting receptacle 1028 around a mounting axis 1030. Mounting axis 1030 is not parallel to pin axes 1026A and 1026B. In the illustrated example, mounting axis 1030 is an axis of symmetry of anti-rotation base 906 relative the curve of bottom surface 1012. Mounting receptacle 1024 extends from top surface 1002 to bottom surface 1012 though anti-rotation base 906. In some examples, mounting receptacle 1024 extend from top surface 1002 to apex 1016 of the curve of bottom surface 1012. Mounting receptacle 1028 is configured to slidably coupled to mounting pin 904 so that, when attached to the patient, mounting pin 904 extends into cavity 1014 though anti-rotation base 906.

Figure 11A:
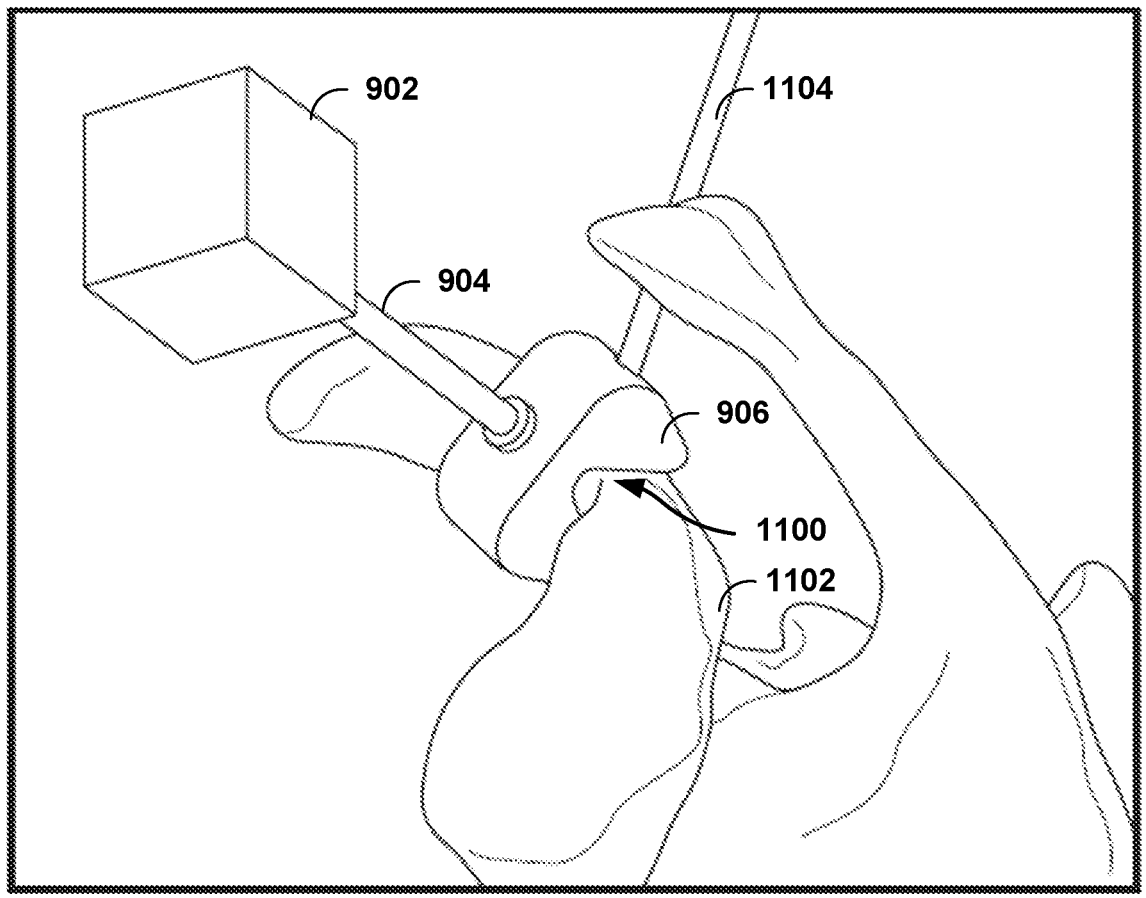
FIGS. 11A and 11B illustrate the registration marker of FIG. 9 resting on and bearing against a surface of a glenoid.
Figure 11B:
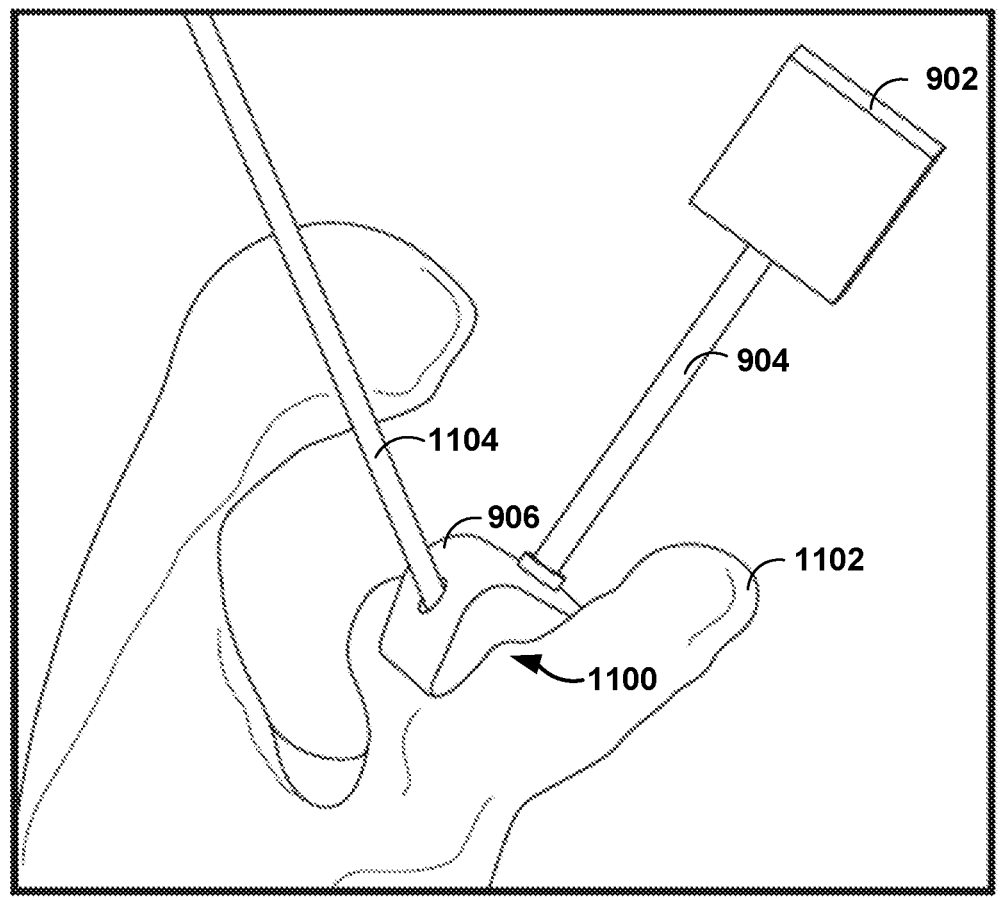
Figure 12:
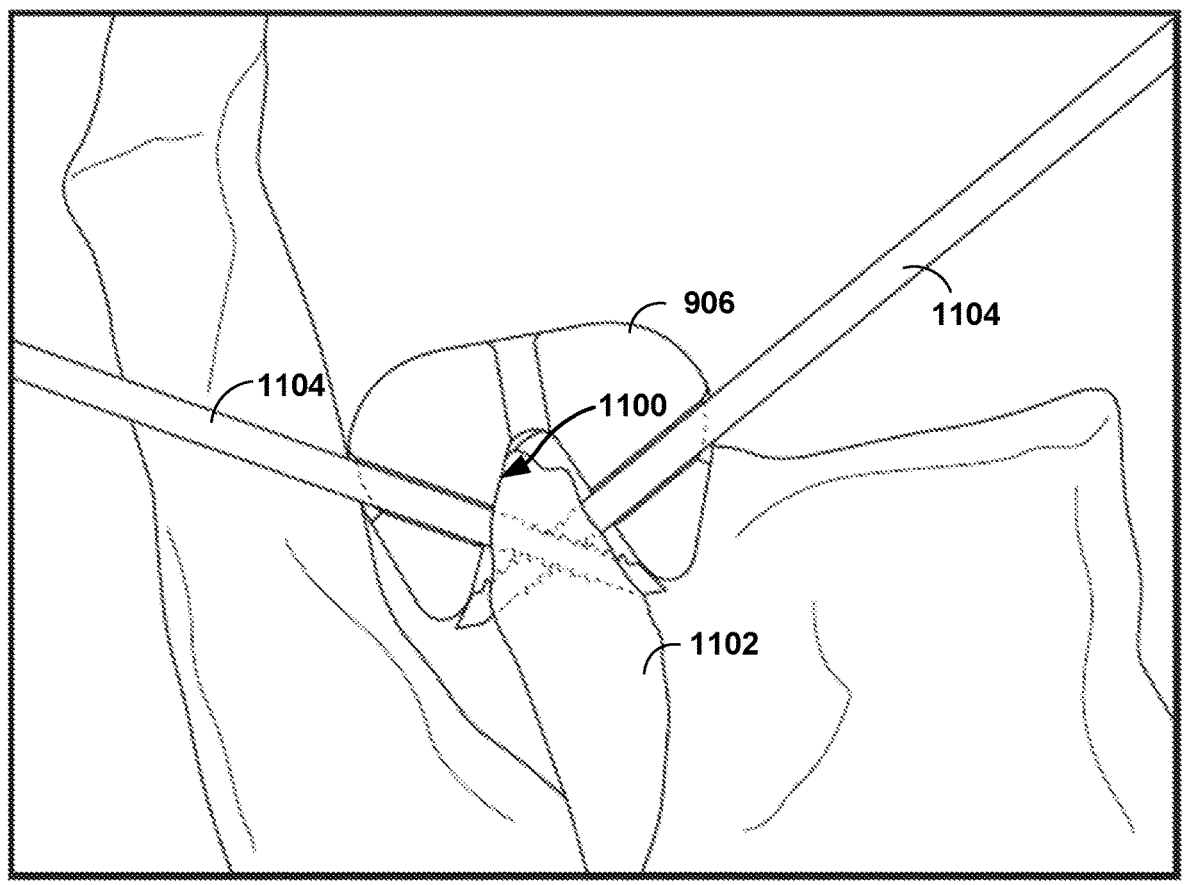
FIG. 12 is cross-section view of an example of an anti-rotation base affixed to a glenoid using pins.

FIGS. 11A and 11B illustrate registration marker 900 of FIG. 9 resting on and bearing against a surface 1100 of a glenoid 1102. In the illustrated example, the anti-rotation base 906 is affixed to glenoid 1102 by one or more pins 1104 configured to screw into glenoid 1102 through pin receptacles 1024 such that glenoid 1102 is within cavity 1014. Pins 1104 fix the orientation of anti-rotation base 906 to prevent movement of registration marker 900. FIG. 12 is cross-section view of anti-rotation base 906 affixed to glenoid 1102 using pins 1104. As illustrated in FIG. 12, when installed, pins 1104 do not interfere with each other. In some examples, when pins 1004 are installed, tips of pins 1004 contacts a side (e.g., side 1020A or side 1020B) of anti-rotation bases 906 opposite the corresponding pin receptacle (e.g., pin receptacles 1024A and 1024B). For example, when installing pin 1004 via pin receptacle 1024A, a surgeon may know pin 1004 is deep enough when the tip of pin 1004 contacts sides 1020B. In such examples, sides 1020A and 1020B may act as depth guides to facilitate attaching anti-rotation base 906 without an explicit pin depth measurement. As illustrated in FIGS. 11A and 11B, mounting rod 904 screws into glenoid 1102 through mounting receptacle 1028. Fiducial marker extends away from glenoid 1102.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

What is claimed is:

1. An anti-rotation base of a registration marker of a mixed reality surgery system, the anti-rotation base comprising:
   a bottom surface configured to rest on and bear against a surface of a process of a bone of a patient, the bottom surface having a curve that defines a first bottom side and a second bottom side;
   a plurality of pin receptacles that each define a respective pin axis, wherein the pin axis of a first pin receptacle of the plurality of pin receptacles is not parallel to the pin axis of a second pin receptacle of the plurality of pin receptacles;
   a mounting receptacle configured to receive the registration marker; and
   a top surface, the mounting receptacle extending from the top surface to the bottom surface, the mounting receptacle defining a mounting axis,
   wherein the pin axis of the first pin receptacle and the pin axis of the second pin receptacle are not parallel to the mounting axis,
   wherein the pin axis of the first pin receptacle and the pin axis of the second pin receptacle are defined such that, when installed, a first anchor rod in the first pin receptacle does not interfere with a second anchor rod in the second pin receptacle,
   wherein the pin axis of the first pin receptacle intersects the second bottom side of the bottom surface such that, when installed, a tip of the first anchor rod in the first pin receptacle contacts the second bottom side of the bottom surface, and
   wherein the pin axis of the second pin receptacle intersects the first bottom side of the bottom surface such that, when installed, a tip of the second anchor rod in the second pin receptacle contacts the first bottom side of the bottom surface.

2. The anti-rotation base of claim 1, wherein the bottom surface defines a cavity configured such that, when attached to the patient, a portion of the bone is within the cavity.

3. The anti-rotation base of claim 2, wherein the cavity is specifically shaped for the patient.

4. The anti-rotation base of claim 2, wherein the cavity has a parabolic shape.

5. The anti-rotation base of claim 1, wherein the bottom surface defines a cavity, and wherein the mounting receptable is configured to slidably coupled to a mounting pin of the registration marker so that, when attached to the patient, the mounting pin extends into the cavity though the anti-rotation base.

6. The anti-rotation base of claim 1, wherein the anti-rotation base defines a cavity and wherein a mounting axis of the mounting receptacle defines define an axis of symmetry of the cavity.

7. The anti-rotation base of claim 1, wherein the bottom surface defines a cavity, and wherein the first pin receptacle is positioned on a first side of the cavity and the second pin receptacle is positioned on a second side of the cavity.

8. The anti-rotation base of claim 1, wherein the bone is a scapula, and wherein the bottom surface is configured to rest on and bear against surface of a coracoid process of the scapula of the patient.

9. An anti-rotation base of a registration marker of a mixed reality surgery system, the anti-rotation base comprising:
   a bottom surface having a curve that defines a first bottom side and a second bottom side, wherein when the anti-rotation base is attached to a patient, the bottom surface straddles a process of a bone of the patient;
   a first side surface;
   a second side surface parallel with the first side surface;
   a first end surface, a first pin receptacle extending from the first end surface to the first bottom side of the bottom surface; and
   a second end surface opposite the first end surface, a second pin receptacle extending from the second end surface to the second bottom side of the bottom surface,
   wherein the first and second pin receptacles each define a respective pin axis, wherein the pin axis of the first pin receptacle is not parallel to the pin axis of the second pin receptacle, wherein the pin axis of the first pin receptacle and the pin axis of the second pin receptacle are defined such that, when installed, a first anchor rod in the first pin receptacle does not interfere with a second anchor rod in the second pin receptacle, wherein the pin axis of the first pin receptacle intersects the second bottom side of the bottom surface such that, when installed, a tip of the first anchor rod in the first pin receptacle contacts the second bottom side of the bottom surface, and wherein the pin axis of the second pin receptacle intersects the first bottom side of the bottom surface such that, when installed, a tip of the second anchor rod in the second pin receptacle contacts the first bottom side of the bottom surface.

10. The anti-rotation base of claim 9, further comprising a top surface, a mounting receptacle extending from the top surface to the bottom surface.

11. The anti-rotation base of claim 10, wherein the mounting receptacle extends from the top surface to an apex of the curve of the bottom surface.

12. The anti-rotation base of claim 9, further comprising a top surface, a mounting receptacle extending from the top surface to the bottom surface, the mounting receptacle defining a mounting axis, wherein the pin axis of the first pin receptacle and the pin axis of the second pin receptacle are not parallel to the mounting axis.

13. The anti-rotation base of claim 9, wherein first and second bottom sides define a cavity configured such that, when the anti-rotation base is attached to the patient, a portion of the bone is within the cavity.

14. The anti-rotation base of claim 13, wherein the cavity has a parabolic shape.

15. The anti-rotation base of claim 13, further comprising a top surface, a mounting receptacle extending from the top surface to the bottom surface, wherein a mounting axis of the mounting receptacle defines define an axis of symmetry of the cavity.

16. A registration marker of a mixed reality surgery system, the registration marker comprising:

a mounting rod;

a fiducial marker comprising a polyhedron having indicia on multiple sides of the polyhedron, the fiducial marker positioned at a distal end of the mounting rod; and an anti-rotation base positioned at a proximal end of the mounting rod, the anti-rotation base comprising:

a bottom surface configured to rest on and bear against a surface of a process of a bone of a patient, the bottom surface having a curve that defines a first bottom side and a second bottom side;

a plurality of pin receptacles that each define a respective pin axis, wherein the pin axis of a first pin receptacle of the plurality of pin receptacles is not parallel to the pin axis of a second pin receptacle of the plurality of pin receptacles;

a mounting receptacle configured to receive the mounting rod; and a top surface, the mounting receptacle extending from the top surface to the bottom surface, the mounting receptacle defining a mounting axis, wherein the pin axis of the first pin receptacle and the pin axis of the second pin receptacle are not parallel to the mounting axis, wherein the pin axis of the first pin receptacle and the pin axis of the second pin receptacle are defined such that, when installed, a first anchor rod in the first pin receptacle does not interfere with a second anchor rod in the second pin receptacle, wherein the pin axis of the first pin receptacle intersects the second bottom side of the bottom surface such that, when installed, a tip of the first anchor rod in the first pin receptacle contacts the second bottom side of the bottom surface, and wherein the pin axis of the second pin receptacle intersects the first bottom side of the bottom surface such that, when installed, a tip of the second anchor rod in the second pin receptacle contacts the first bottom side of the bottom surface.

* * * * *